United States Patent
Widmann et al.

(10) Patent No.: US 10,605,732 B2
(45) Date of Patent: Mar. 31, 2020

(54) PORTABLE DEVICE FOR DETECTING EXPLOSIVE SUBSTANCES COMPRISING A DEVICE FOR GENERATING AND MEASURING THE EMISSION OF AN INDICATOR

(71) Applicant: Institut Dr. Foerster GmbH & Co. KG, Reutlingen (DE)

(72) Inventors: Stefan Widmann, Hechingen (DE); Gert Sinn, Berlin (DE); Klaus-Henrik Mittenzwey, Berlin (DE)

(73) Assignee: Institut Dr. Foerster GmbH & Co. KG, Reutlingen (DE)

( * ) Notice: Subject to any disclaimer, the term of this patent is extended or adjusted under 35 U.S.C. 154(b) by 0 days.

(21) Appl. No.: 16/034,219

(22) Filed: Jul. 12, 2018

(65) Prior Publication Data

US 2019/0049376 A1 Feb. 14, 2019

Related U.S. Application Data

(63) Continuation of application No. PCT/EP2017/050590, filed on Jan. 12, 2017.

(30) Foreign Application Priority Data

Jan. 13, 2016 (DE) ........................ 10 2016 200 271

(51) Int. Cl.
  *G01N 21/64* (2006.01)
  *G01N 33/00* (2006.01)
  (Continued)

(52) U.S. Cl.
  CPC ....... *G01N 21/643* (2013.01); *G01N 21/6452* (2013.01); *G01N 21/76* (2013.01);
  (Continued)

(58) Field of Classification Search
  CPC .. G01N 21/643; G01N 21/6452; G01N 21/76; G01N 21/783; G01N 33/0057;
  (Continued)

(56) References Cited

U.S. PATENT DOCUMENTS 5,589,351 A 12/1996 Harootunian
6,104,945 A 8/2000 Modell et al.
(Continued)

FOREIGN PATENT DOCUMENTS

DE 101 31 687 A1 1/2003
DE 699 13 257 T2 9/2004
(Continued)

OTHER PUBLICATIONS

International Search Report (PCT/ISA/210) issued in PCT Application No. PCT/EP2017/050590 dated Apr. 24, 2017 with English translation (six (6) pages).
(Continued)

*Primary Examiner* — Mark R Gaworecki
(74) *Attorney, Agent, or Firm* — Crowell & Moring LLP

(57) ABSTRACT

A portable appliance detects explosive materials. An indicator has a carrier and a plurality of indicator substances arranged in different regions to represent a location dependent pattern. The indicator substances are a thin layer positionable in an indicator area by a holding apparatus. A plurality of radiation sources emit quasi-monochromatic excitation radiation and are arranged at various locations in a radiation area so as to represent a location dependent pattern of radiation sources. An excitation beam path with a first imaging system images excitation radiation into the indicator area such that emission of the indicator substances is producible at the imaging locations on the indicator area. An emission beam path with a second imaging system images the indicator area into a reception area such that a
(Continued)

pattern of emissions is producible depending on the location. Receivers receive emissions from the reception area and convert them into electrical signals.

22 Claims, 7 Drawing Sheets

(51) Int. Cl.
*G01N 21/76* (2006.01)
*G01N 21/77* (2006.01)
*G01N 21/78* (2006.01)

(52) U.S. Cl.
CPC ....... *G01N 33/0057* (2013.01); *G01N 21/783* (2013.01); *G01N 2021/6432* (2013.01); *G01N 2021/7786* (2013.01); *G01N 2021/7793* (2013.01); *G01N 2201/0221* (2013.01); *G01N 2201/0627* (2013.01); *G01N 2201/0631* (2013.01)

(58) Field of Classification Search
CPC ... G01N 2021/6432; G01N 2021/7786; G01N 2021/7793; G01N 2201/0221; G01N 2201/0627; G01N 2201/0631
See application file for complete search history.

(56) References Cited

U.S. PATENT DOCUMENTS

| | | |
|---|---|---|
| 6,197,503 B1 | 3/2001 | Vo-Dinh et al. |
| 6,372,183 B1 | 4/2002 | Akong et al. |
| 6,852,986 B2 | 2/2005 | Lee et al. |
| 6,967,103 B2 | 11/2005 | Schwartz et al. |
| 7,102,131 B2 | 9/2006 | Spolaczyk et al. |
| 7,142,290 B2 | 11/2006 | Tsien et al. |
| 7,369,227 B2 | 5/2008 | Gutekunst et al. |
| 7,414,724 B2 | 8/2008 | Eckert et al. |
| 7,595,473 B2 | 9/2009 | Walt et al. |
| 8,101,897 B2 | 1/2012 | Schirr et al. |
| 8,287,811 B1 | 10/2012 | Harper et al. |
| 8,323,576 B2 | 12/2012 | Aker et al. |
| 8,374,802 B2 | 2/2013 | Treptow et al. |
| 8,597,485 B2 | 12/2013 | Amirkhanian et al. |
| 8,674,325 B2 | 3/2014 | Schliesser et al. |
| 9,089,828 B2 | 7/2015 | Howell et al. |
| 2004/0063168 A1 | 4/2004 | Wiles et al. |
| 2004/0106211 A1 | 6/2004 | Kauer et al. |
| 2006/0109475 A1 | 5/2006 | Misener et al. |
| 2007/0243107 A1 | 10/2007 | Chase et al. |
| 2008/0206846 A1 | 8/2008 | Tasch et al. |
| 2008/0210700 A1 | 9/2008 | Tasch et al. |
| 2009/0218518 A1 | 9/2009 | Schirr et al. |
| 2009/0324446 A1 | 12/2009 | Schanze et al. |
| 2010/0027005 A1 | 2/2010 | Ogura |
| 2010/0320364 A1 | 12/2010 | Unger et al. |
| 2014/0017803 A1 | 1/2014 | Deans et al. |
| 2014/0065720 A1 | 3/2014 | Ja |
| 2014/0315226 A1 | 10/2014 | Matthias et al. |
| 2016/0305881 A1 | 10/2016 | Boege et al. |
| 2017/0102335 A1 | 4/2017 | Suslick et al. |

FOREIGN PATENT DOCUMENTS

| | | |
|---|---|---|
| DE | 10 2004 056 787 A1 | 6/2006 |
| DE | 10 2005 027 055 B3 | 10/2006 |
| DE | 10 2005 027 407 B3 | 11/2006 |
| DE | 10 2005 046 583 A1 | 3/2007 |
| DE | 10 2006 036 171 A1 | 1/2008 |
| DE | 10 2006 048 346 A1 | 4/2008 |
| DE | 10 2007 062 250 A1 | 6/2009 |
| DE | 10 2011 117 320 A1 | 5/2013 |
| DE | 20 2010 018 011 U1 | 8/2013 |
| EP | 0 953 838 A1 | 11/1999 |
| EP | 2 081 011 A1 | 7/2009 |
| GB | 2500177 A | 9/2013 |
| KR | 2003-0040830 A | 5/2003 |
| WO | WO 93/13423 A1 | 7/1993 |
| WO | WO 01/86263 A2 | 11/2001 |
| WO | WO 02/059592 A2 | 8/2002 |
| WO | WO 03/031953 A2 | 4/2003 |
| WO | WO 2006/052682 A2 | 5/2006 |
| WO | WO 2007/031203 A1 | 3/2007 |
| WO | WO 2007/036281 A1 | 4/2007 |
| WO | WO 2008/043541 A2 | 4/2008 |
| WO | WO 2008/051189 A2 | 5/2008 |
| WO | WO 2009/027102 A2 | 3/2009 |
| WO | WO 2010/082582 A1 | 7/2010 |
| WO | WO 2012/134436 A1 | 10/2012 |
| WO | WO 2015/191510 A1 | 12/2015 |

OTHER PUBLICATIONS

German-language Written Opinion (PCT/ISA/237) issued in PCT Application No. PCT/EP2017/050590 dated Apr. 24, 2017 (nine (9) pages).

Xin et al., "A Portable Fluorescence Detector for Fast Ultra Trace Detection of Explosive Vapors," Review of Scientific Instruments, Oct. 2011, pp. 1-8, vol. 82, No. 10, American Institute of Physics, XP12152051A, (eight (8) pages).

PORTABLE DEVICE FOR DETECTING EXPLOSIVE SUBSTANCES COMPRISING A DEVICE FOR GENERATING AND MEASURING THE EMISSION OF AN INDICATOR

This application is a continuation of PCT International Application No. PCT/EP2017/050590, filed Jan. 12, 2017, which claims priority under 35 U.S.C. § 119 from German Patent Application No. 10 2016 200 271.6, filed Jan. 13, 2016, the entire disclosures of which are herein expressly incorporated by reference.

BACKGROUND AND SUMMARY OF THE INVENTION

The invention relates to a portable appliance for detecting explosive materials, having an apparatus for generating and measuring emission of an indicator.

By way of example, the emission can be produced by excitation with radiation (fluorescence, phosphorescence) or by a chemical reaction (chemiluminescence). The focus is on the generation and measurement of the emission of indicator substances that are applied to a carrier. By way of example, a carrier can be a glass or a plastic on which the indicator substances (one or more) are applied as a thin layer. By way of example, indicator substances can be fluorescence-capable polymer molecules, the fluorescence of which changes after contacting certain analytes. Analytes are compounds, materials or substances about which a statement should be made within the scope of a measurement. The change in the fluorescence of the indicator substance is a clue about the existence of the analyte, or else a measure of the concentration thereof. The system with carrier and indicator substance is referred to as indicator below.

Apparatuses of this type have been known for a relatively long time and they are used, for example, in the field of detecting analytes such as explosive materials and other substances (drugs, toxic gases, and more) that are relevant to health and the environment. The indicator is contacted under defined conditions with the medium to be examined, the latter possibly being gaseous, for example. If explosive materials, for example, are situated in the medium, they are able to change the emission of the indicator.

WO 03/031953 presents an optical unit in which an indicator substance is situated as a layer on the radiation source for exciting the emission. Here, the radiation source is a GaN-LED. This emission reaches a detector via an optical filter, said detector capturing the emission in the forward direction.

U.S. Pat. No. 8,287,811 B1 presents an optical unit that contains an indicator with two indicator substances on a common carrier. The two indicator substances are applied to the two opposite sides of the carrier. Both indicator substances are irradiated with the same wavelength in the UV range. Quenching occurs if the one indicator substance is contacted by the analyte. The fluorescence of the other indicator substance is used as a reference signal. The fluorescences are steered in the direction of a lens onto a photomultiplier. A filter wheel with three filters is arranged in front of the photomultiplier.

U.S. Pat. No. 8,323,576 B2 describes an appliance system, the core of which is a cylindrical solid which may consist of glass, for example. This body is embodied as a capillary and heatable in a defined fashion. The capillary is divided into two. The first part serves as a gas inlet and as an adsorption and desorption section for the analytes to be detected. A second part contains an optical unit with an indicator substance applied to the inner wall. The indicator is impinged upon by a radiation source via a wavelength-selective filter. The measurement of the emission is carried out as a transmitted light measurement via the filter and receiver.

WO 2012/134436 A1 describes an indicator which likewise is embodied as a capillary and a common carrier for a plurality of indicator substances. In addition to the fluorescence, phosphorescence and chemiluminescence also come into question as emission signals. In one example, the capillary contains two indicator substances, which are each irradiated by a 405 nm LED. The measurement of the emission is carried out via filters and receivers. Here, the indicator itself serves as an optical waveguide.

WO 01/86263 A2 proposes an apparatus in which the excitation radiation of the radiation source is coupled into an optical waveguide, embodied as a splitter, via a filter and guided to the optical waveguide end face. A polymer that ensures an accumulation of the analyte is applied to this end face. Some of the emission is returned to the splitter by the same optical waveguide and steered onto a detector with a filter. The apparatus allows a plurality of such optical waveguide arrangements to be received. Hence, the overall system may have different excitation sources, filters, polymers and detectors.

In US 2014/0065720 A1, the fluorescence is produced by way of the surface plasmon-coupled emission (SPCE) method. The fluorescence is captured with a high signal-to-noise ratio, and so it can be measured with a high spectral resolution. For the purposes of carrying out the SPCE method, the indicator additionally contains a metal layer and a dielectric layer. The sensor is presented with a radiation source for excitation radiation.

In WO 2008/051189 A2, a fluorescence system is presented, said fluorescence system being equipped with filter wheels on both the excitation side and the emission side for the purposes of the spectral resolution. Many excitation and emission wavelengths are available using such a system.

The appliances should be suitable for detecting analytes such as explosive materials and other substances that are relevant to health and the environment. In part, they are equipped with great technical functionality and have a correspondingly complex structure. In another part, the appliances contain minimalized technical equipment.

It is an object of the invention to provide a fieldcapable, portable appliance having an apparatus for generating and measuring an emission for use in the detection of explosive materials, said appliance being well adapted to the application in harsh environments, being easily handled by an operator, having a relatively simple, robust structure and nevertheless being characterized by a high measuring certainty.

This object is achieved by a portable appliance in accordance with embodiments of the invention. Advantageous developments are set forth and claimed herein. The phrasing of all the claims is incorporated into the content of the description by reference.

On account of its structure, the portable appliance is suitable for detecting explosive materials by measuring optical emissions. To this end, use is made of appropriate indicators that react sensitively to these substances, the changes of said indicators being optically detectable by the presence of the searched-for analytes. Optionally, it is also possible to detect other substances that are relevant to health and the environment (such as, for example, drugs, toxic gases and more). To this end, use may possibly be made of other indicators. The apparatus for generating and measuring emission of an indicator is an essential functional constituent part of the appliance.

The apparatus for generating and measuring emission has a plurality of radiation sources, which can each emit quasi-monochromatic excitation radiation. In this application, the phrase "quasi-monochromatic excitation radiation" denotes excitation radiation from a relatively narrow wavelength range, for example with a spectral bandwidth of significantly less than 100 nm, wherein the spectral bandwidth may be of the order of approximately 10 nm or a few 10 nm, for example. The excitation radiation may also be referred to as "narrow bandwidth excitation radiation". Then, the term "excitation wavelength" relates to a relatively narrow wavelength range. Consequently, the excitation radiation is not broadband white light, in particular. By way of example, light-emitting diodes (LEDs) or laser diodes can be used as radiation sources for producing the excitation radiation, or else broadband white light sources, the radiation of which is guided via at least one wavelength-selective device (e.g. a grating or a narrow bandwidth filter).

Consequently, the excitation is not performed using a continuous broadband spectrum (e.g. by means of white light), but in a single narrow bandwidth wavelength range or in a plurality of spectrally different, relatively narrow bandwidth wavelength ranges.

The radiation sources are arranged in a defined spatial arrangement with mutual spacing from one another. The spatial distribution of the radiation sources in the radiation area determines the location-dependent pattern of radiation sources, which can be used for the measurement.

The excitation light reaches the indicator area via an excitation beam path. To this end, the excitation beam path has at least one first imaging system. Then, emissions of the indicator substances can be produced at the locations at which the excitation radiation is imaged via the excitation beam path on the indicator area or onto the indicator area. Then, these locations form a pattern depending on the location in the indicator area. The pattern of these locations may correspond to the pattern of the radiation sources within the meaning of a geometric similarity, but this is not mandatory. A plurality of laterally distributed locations can be impinged upon by excitation radiation in the indicator area. The local distribution of the excitation radiation on the indicator area and the local distribution of the indicator substances are matched to one another.

An emission beam path serves to image the indicator area into a reception area in such a way that a pattern of emissions is producible in the reception area depending on the location. Thus, emissions can strike at different locations of the reception area. To this end, the emission beam path has at least one second imaging system. The pattern of emissions in the reception area may correspond to the pattern of locations of the indicator area, impinged upon by excitation radiation, within the meaning of a geometric similarity, but this is not mandatory.

If reference is made to an "imaging system" or an imaging optical unit within the scope of this application, this should mean that the imaging system can produce a magnified, reduced or a 1:1 image of an object without, in the process, modifying the form or the appearance of the object (apart from aberrations). The area or plane on which imaging takes place may, in the process, lie in an image plane of the imaging system or outside of the image plane.

A plurality of receivers are provided for receiving emissions from the reception area and for converting the received emissions into electrical signals. Here, a receiver is assigned to at most one indicator substance within the meaning of, at a given time, there not being two or more indicator substances that are assigned the same receiver. Consequently, at a given time, a receiver receives emission radiation from at most exactly one indicator substance assigned thereto. The emissions in the entrance area are locally decoupled from one another in such a way that the emissions are resolvable without mutual superposition of emissions. The emission received by a receiver can be assigned to exactly one of the indicator substances and one of the radiation sources. As a result of this, highly selective measurements with a high measurement accuracy are possible. A receiver can be optically adjusted in an ideal fashion to only the one indicator substance assigned thereto. As a result, ideal matching of the area (extent, form and size of the area) of the indicator substance to the active area of the receiver becomes possible. As result, it is possible to obtain a high signal-to-noise ratio (S/N ratio).

The appliance is designed as a portable appliance that can easily be carried and operated by a single person. In particular, the appliance can be constructed to be so small and light that it can be held in only one hand during use (hand-held appliance). Installation size and mass, and the robustness of the components installed therein, are optimized in view of this application. By way of example, the mass may be less than 2 kilograms, in particular less than 1.5 kilograms, but usually at least 0.5 kilograms. The installation size including the holding device for the indicator may be e.g. 50 cm or less, or 40 cm or less, or 30 cm or less (measured in the direction of greatest extent), with the installation size usually being at least 10 cm to 15 cm, however.

Even though, in principle, it is possible to arrange the excitation beam path and the emission beam path on different sides of the indicator area, provision is preferably made for the excitation beam path and the emission beam path to be arranged in a backward geometry such that the excitation beam path and the emission beam path are arranged on one and the same side of the indicator area or indicator. In this way, it is particularly easily possible to house the indicator in a holding apparatus that can be coupled to one side of the appliance and can easily be interchanged when required. The backward geometry may also be expedient in the case of a holding apparatus that is securely integrated into the appliance since, for example, all optical components can be housed on the same side of the indicator area.

The measurement geometry can be set by the structure in such a way that excitation radiation that has undergone specular reflection at the indicator, and hence radiation disturbing the emission measurement, does not strike the reception area to a relevant extent and hence is not able to reach a receiver either and increase the noise background there. In preferred embodiments, different angles of excitation radiation and emission radiation in relation to the surface normal of the indicator are provided in the region where the excitation radiation strikes for the purposes of avoiding or reducing the entrance into the emission beam path of intensity components of the excitation radiation that underwent specular reflection.

Preferably, this is achieved by virtue of optical axes of one or more or all imaging systems of the excitation beam path (first imaging system) and of the emission beam path (second imaging system) running obliquely in relation to one another in the region of the indicator area and not being arranged symmetrically in relation to the surface normal. By way of example, an angle between incident excitation radiation and emitted emission radiation may lie in the range from 20° to 60°, in particular in the range from 30° to 50°.

Preferably, no physical beam splitter (such as a dichroic mirror or a polarization beam splitter, for example) or geometric beam splitter (such as a mirror with at least one breach in the illuminated region, for example) is required for separating excitation beam path and emission beam path, and hence neither is provided either. This renders it possible to avoid typical problems that may arise when using beam splitters, for example stray light generated at the beam splitter.

The arrangement of excitation beam path and emission beam path may be such that optical axes of one or more or all imaging systems of the excitation beam path (first imaging system or first imaging systems) and one or more or all imaging systems of the emission beam path (second imaging system or second imaging systems) cross at a distance in front of the indicator area, and so points of intersection of the optical axes in the indicator area are laterally spaced apart. As a result, it is possible to ensure that excitation radiation, which undergoes specular reflection at one or more at least partly reflecting interfaces of the indicator (e.g. airindicator interface), practically cannot reach into the emission beam path and hence cannot reach the receivers. This contributes to being able to dispense with the use of excitation filters and/or emission filters, where applicable. The distance lies significantly outside of the manufacturing tolerances and may lie, for example, in the range from 1 mm to 10 mm, optionally also thereabove or therebelow.

Some embodiments are characterized by a wavelength-selective device with an entrance area and an exit area, wherein the entrance area can be impinged upon by the emission received in the reception area and the receivers are arranged in the exit area. As a result of this, it is possible to select certain narrower wavelength ranges from a broader emission spectrum, or choose these for the evaluation. The same wavelength range may be chosen for all receivers. It is also possible to choose different wavelength ranges that have a spectral distance from one another for different receivers. The wavelength-selective device may be interchangeable in order to be able to adapt the appliance in an ideal fashion to different measurement problems. However, a wavelength-selective device between the reception area and the receivers is not mandatory.

A separate receiver may be assigned to each indicator substance. Interstices without light-sensitive areas may lie between the receivers. The receivers may be individually adjustable or adjustable separately from one another such that each measurement channel can be set in an optimized fashion for its measurement problem. The number of receivers may correspond to the number of effectively employable excitation channels.

Preferably, provision is made for one or more radiation sources to be assigned to each indicator substance, wherein a radiation source is assigned to at most one indicator substance, and so there are not two or more indicator substances that are assigned the same radiation source. As a result, the radiation source can be optically adjusted in an ideal fashion to only the one indicator substance assigned thereto. As a result, an ideal matching of the area of the indicator substance to that of the radiation source is possible. This is conducive to obtaining a high signal-to-noise ratio.

In many embodiments, photomultipliers that have high sensitivities even in the case of low measurement-relevant intensities are used as receivers. In particular, it is possible to use semiconductor-based photomultipliers, e.g. Si-photo-multipliers (Si-PMTs). These are mechanically robust, relatively insensitive to tremors and offer very high sensitivities in the case of relatively small sensitive areas. Alternatively, it is also possible to use e.g. conventional photomultipliers or photodiodes as receivers.

As mentioned, an imaging system can produce a magnified, reduced or a 1:1 image of an object without, in the process, modifying the form or the appearance of the object (apart from aberrations). The area or plane on which imaging takes place may, in the process, lie in an image plane of the imaging system or outside of the image plane. If reference is made to "non-imaging optics", this should mean that the employed optical elements (one or more) act as beam shapers that can change the form or the appearance of an object. Imaging optics and non-imaging optics can be combined in an optical channel (excitation channel or emission channel).

It is possible to construct the apparatus in such a way that the excitation beam path only has a single excitation channel with a first imaging system, to which two or more radiation sources are then assigned. The excitation channel may provide a plurality of sub-channels for the excitation radiation propagating from the radiation sources to the indicator area, with a common optical axis.

By contrast, many embodiments are constructed in such a way that the excitation beam path has a plurality of excitation channels, i.e. two or more excitation channels, wherein each excitation channel has a first imaging system that defines an optical axis of the corresponding excitation channel. By way of example, the number of mutually separate excitation channels may lie in the range from two to ten, in particular in the range from three to six. Hence, the excitation radiation from different radiation sources can be guided to the indicator on separate excitation channels that are optically separated from one another. As a result, there is structural prevention of cross talk between the excitation channels.

In this application, the term "excitation channel" denotes an optical system having at least one optical element configured with refractive power, for example a lens, and optionally further optical elements, such as e.g. at least one beam shaper and/or at least one filter. An excitation channel guides radiation from one or more radiation sources into the indicator area in a defined manner.

The arrangement may be such that provision is made of exactly one excitation channel for each indicator region, and so the number of excitation channels corresponds to the number of indicator regions. The term "indicator region" denotes the location of the indicator substance or the region in which an indicator substance is situated. It is also possible to use an excitation channel for guiding excitation radiation to two or more indicator regions that are separate from one another.

Likewise, a plurality of mutually separate emission channels may be provided for the emission beam path.

By contrast, provision is made in one embodiment for the emission beam path to have a common imaging system (second imaging system) for all emissions, said imaging system defining an optical axis of the emission beam path. Thus, a single emission channel may suffice. It may provide a plurality of sub-channels for the emissions propagating from the indicator to the reception plane in the case of a common optical axis.

In one embodiment with a plurality of excitation channels, the excitation channels form a symmetric arrangement in relation to the emission channel. In particular, the arrangement may be mirror symmetric in relation to at least one symmetry plane that contains the optical axis of the emission beam path.

In an embodiment with a plurality of excitation channels, the excitation channels and the emission channel form a conical arrangement, wherein optical axes of the excitation channels are arranged on a lateral conical face that surrounds the emission channel and the optical axis of the emission channel is arranged along the axis of the cone. As a result of this, a plurality of radiation-guiding channels with very compact dimensions can be provided between the radiation sources, the indicator and the reception plane or the receivers. In preferred embodiments, the cone tip of the conical arrangement, i.e. the point of intersection of the optical axes of the excitation channels, does not lie in the indicator area but at a distance therefrom, in particular in front of the indicator area.

In some cases, it may be expedient for a beam shaper to be arranged in an excitation channel between a radiation source and the indicator plane. Here, in general, the term "beam shaper" denotes non-imaging optics which are able to change the form or the appearance of an object. By way of example, a beam shaper can have a diffuser function. By way of example, the beam shaper can have a microstructured component (e.g. a diffractive optical element) and/or it may be designed to convert a non-uniform intensity profile into a uniform and steep intensity profile. As a result of this, it is possible to obtain a uniform or homogeneous illumination of regions to be excited (spots) of the indicator substances, even if use is made of small, quasi-punctiform radiation sources with a non-uniform emission characteristic, as a result of which meaningful quantitative comparisons can be facilitated and the measurement accuracy can be increased.

In some embodiments, provision is made of a clock for actuating radiation sources, wherein the clock is configured in such a way that all radiation sources are clocked sequentially in series or that some of the radiation sources or all radiation sources are clocked simultaneously or that radiation sources are clocked alternately. As a result, the radiation sources can work in flash operation, and so they can be activated and deactivated in a temporally defined manner by way of a clock generator. These variants can be described in such a way that the radiation area does not only represent a pattern of radiation sources depending on location, but also a pattern depending on time. In this case, a pattern can always be present whenever at least one dependence (location, time) exists.

With the aid of a clock, it is also possible to produce a secondary or virtual radiation source in an excitation channel, said secondary or virtual radiation source being able to selectively emit different excitation wavelengths. In some embodiments, two or more radiation sources for emitting different excitation wavelengths are assigned to at least one of the excitation channels, wherein the radiation sources are alternately clockable by means of a clock and a radiation merging device is provided for selective input coupling of excitation radiation from the radiation sources into the excitation channel. By way of example, the radiation merging device can have a beam shaper in the form of a diffuser.

In some embodiments, a particularly compact and robust configuration is achieved by virtue of all optical elements of the apparatus, i.e. all optical elements of the excitation beam path and of the emission beam path, being installed or integrated into a single component. The component may serve as an optics holder for all optical elements. It may consist of a single piece (monolithic component) or else it may be securely assembled from two, three or more components. By way of example, such a component can be produced as an injection-molded part or else by sintering or by material-ablating processing from the whole. All components in the apparatus that are able to spatially, temporally and spectrally modify the properties of radiation are considered to be optical elements. Predominantly, these are the functions of imaging, steering and guiding, and of shaping the radiation. As a result of the combined housing of all optical elements in one and the same component that serves as an optics holder, the relative arrangement of the optical elements is continuously maintained, even in the case of relatively strong movements of the entire apparatus, in the case of jolts or tremors. Thus, the appliance can also be used in harsh environments; measurements with a high accuracy are possible even when an operator holds the appliance with one hand and the entire appliance is easily moved as a result thereof.

Preferably, a plurality of receiving channels for receiving the optical elements of at least one excitation channel and one emission channel are formed in the component. The receiving channels, which can be introduced into an initially solid component by way of drilling or electrical discharge machining, for example, may each have a rotationally symmetric form, for example; other cross-sectional shapes are likewise possible. Preferably, the optical elements are mounted individually or in groups in mounting elements, e.g. sleeve-shaped mounting elements, that fit into assigned portions of the receiving channels in the component and which can be inserted into the receiving channels and can be anchored there when assembling the apparatus.

An appliance that is specifically configured for detecting explosive materials preferably has an evaluation device, connected to the receivers, for receiving electrical signals of the receivers and for evaluating the spectral information about the emissions contained in the signals, wherein the evaluation device is configured in such a way that at least one of the following information items is establishable and can be output to an operator or user of the information: information items about the amount of one or more searched-for analytes; information about the type of one or more analytes.

Here, the analytes respectively comprise one or more explosive materials or groups of explosive materials. Information about spectral characteristics of fluorescence spectra and/or luminescence spectra of the target substances may be stored in the form of target substance data in a memory of the evaluation device, it being possible to resort to said data for comparison operations within the scope of the evaluation.

The invention also relates to the use of the appliance for detecting explosive materials, wherein use is made of an indicator that has at least one indicator substance which, in the case of irradiation by excitation radiation and contact with an analyte containing at least one explosive material, exhibits a reduction or increase in the fluorescence intensity emitted by the indicator substance.

Other objects, advantages and novel features of the present invention will become apparent from the following detailed description of one or more preferred embodiments when considered in conjunction with the accompanying drawings.

BRIEF DESCRIPTION OF THE DRAWINGS

FIGS. 6 to 12 show schematic spatial distributions or patterns of radiation sources, irradiated areas and emissions in various successively marked areas along the beam paths of different examples.

DETAILED DESCRIPTION OF THE EXEMPLARY EMBODIMENTS

In the following presentation of exemplary embodiments, components that are structurally and/or functionally the same or structurally and/or functionally corresponding to one another are occasionally denoted by the same reference signs for reasons of clarity, even if they belong to different exemplary embodiments or can be used there.

Figure 1:
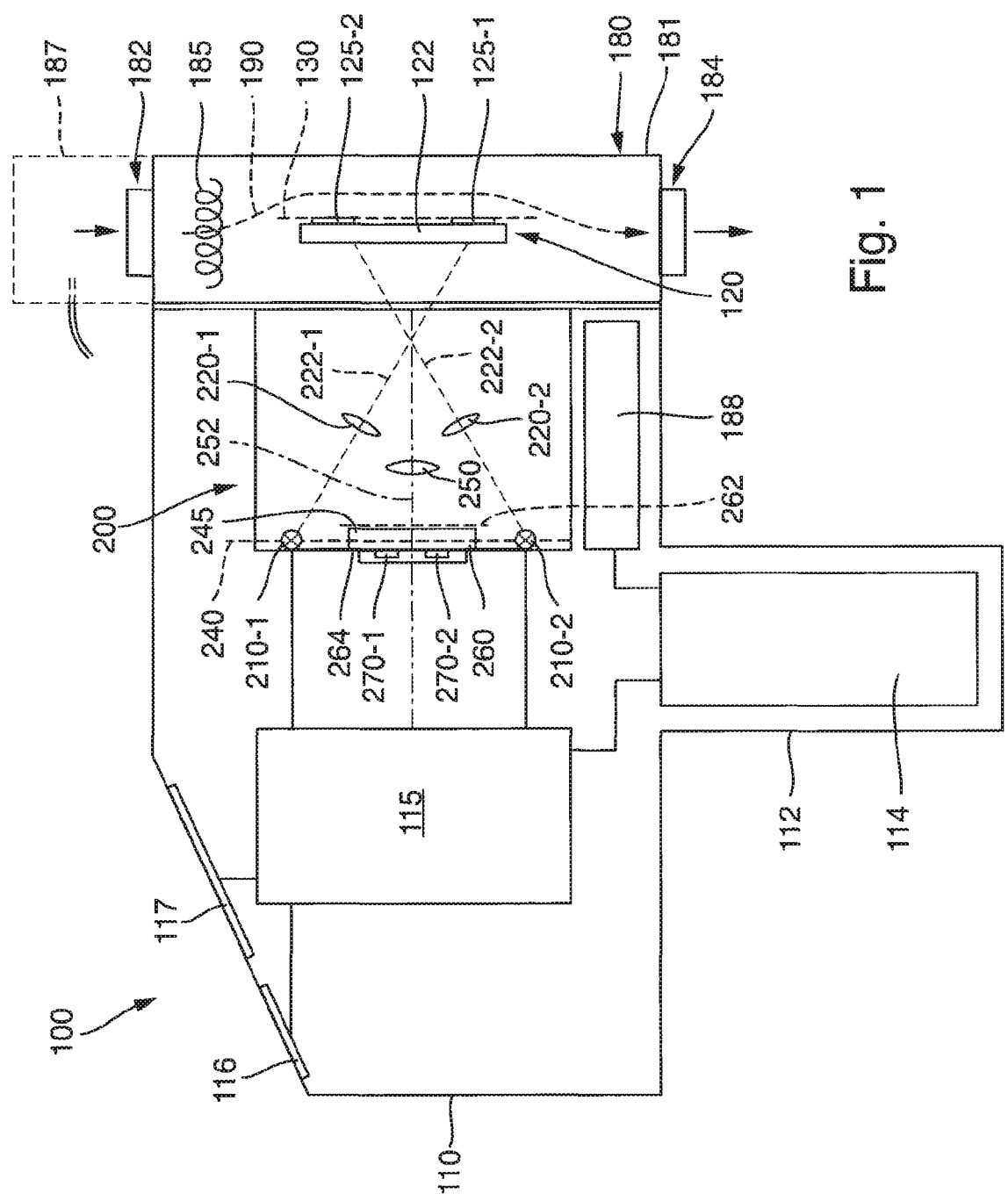
FIG. 1 schematically shows an exemplary embodiment of a portable appliance for detecting explosive materials with the aid of fluorescence measurements.

FIG. 1 schematically illustrates an exemplary embodiment of an appliance 100 for detecting explosive materials. To this end, the appliance uses, inter alia, fluorescence measurements, i.e. optical methods.

This is a portable appliance which, in particular, can be held and carried by only one hand of an operator (hand-held appliance). Preferred fields of application lie, for example, in the field of baggage checks, vehicle checks, checks on persons and/or checks on buildings for explosive materials. The appliance can be used within and outside of buildings, for example in the case of temporally restricted individual checks and/or spot checks. In many cases, it may serve as a replacement for the use of sniffer dogs.

The appliance has a stable, light-tight housing 110 which may consist of, for example, metal, an impact resistant plastic or a combination of these materials. The housing serves for handling the appliance and for holding and protecting the components housed thereon and therein.

A handle portion 112 is attached or formed on the lower side of the housing 110 of the appliance. It serves to handle the appliance with one hand. By way of example, a battery pack or an accumulator pack or any other mains-independent electrical power supply 114 may be housed within the handle portion 112. A control unit 115 with one or more microcontrollers contains all electrical and electronic components that are required for controlling the functions of the appliance. An evaluation device is also integrated into the control unit. The appliance is operated by way of a control panel 116 that is applied to the upper side of the housing. User information can be displayed by a display device 117. It is possible to realize the control panel and the display device by way of a touch-sensitive screen (touchscreen).

An apparatus 200 for generating and measuring emissions of an indicator 120 is arranged in the front part of the housing 110. The indicator has a carrier 122 which, in the exemplary case, consists of a plane-parallel plate made of glass or a plastic that is transparent to the employed radiation (visible spectrum and near UV spectrum). The carrier may be integral (monolithic), like in the exemplary case, or it may be composed from a plurality of components.

A plurality of indicator substances 125-1, 125-2, etc., are applied, respectively as a thin layer, to the carrier 122 on the side of the carrier facing away from the apparatus 200 (rear side). The indicator substances can be applied directly onto a face of the carrier. It is also possible to provide a transparent intermediate layer, which can then be considered to be part of the carrier.

A fluid, in particular gaseous, analyte 190 can impinge upon, or be brought into contact with, the indicator substances.

The indicator is housed in a holding apparatus 180 and held there in a precisely defined position. The holding apparatus 180 itself is attached in an interchangeable manner to the housing 110 of the appliance 100. In other embodiments, a holding apparatus is integrated into the appliance and not interchangeable itself, although the indicator is interchangeable. In the primed assembled state of the appliance illustrated (with a coupled holding apparatus 180 and an indicator 120 housed therein), the indicator substances 125-1, 125-2 are positioned precisely in an indicator area 130 which, in the exemplary case, is a plane area that can also be referred to as an indicator plane. As already shown in schematic FIG. 1, the indicator substances 125-1, 125-2 are arranged in different, i.e. mutually spatially separated, regions of the carrier 122 in such a way that the indicator substances in the indicator area 130 represent a pattern of indicator substances depending on location. The respective spatially restricted indicator substances that have been applied over a relatively small area are thus positioned in well-defined positions within the indicator area 130. By way of example, the indicator substances can be arranged, along a circle around a center, in the form of circular small-area coatings with a few millimeters diameter (see FIG. 2). They can be applied directly on the carrier or with the interposition of a transparent intermediate layer.

The holding apparatus 180 has a dedicated housing 181 and can be removed from the housing 110 and can be coupled thereto in a precisely predeterminable position. The holding apparatus 180 has a delivery air connector 182 with an inlet opening for suctioning gaseous media, which carry the searched-for analyte or analytes. With the aid of a heating device 185, it is possible to heat the suctioned medium to suitable temperatures prior to contact with the indicator substances. The optionally temperature-controlled medium with the analytes is then guided over the indicator substances with the aid of a suitable, preferably heatable fluid channel system and, after contact with said analytes, output from the holding apparatus 180 by way of an exhaust air connector 184.

A wipe sample module 187 that is equipped with dedicated heating can be coupled to the delivery air side of the holding apparatus 180, said wipe sample module being used to supply analytes that were received by way of wipe samples to the delivery air. The flow of the analyte through the fluid channel system of the holding apparatus is produced by means of an electric pump 188, which is connected to the power supply 114 and housed in the housing 110.

In the longitudinal direction shown in FIG. 1 (from left to right), the appliance including the holding apparatus 180 for the indicator 120 applied thereto is no longer than 40 centimeters. The appliance weighs less than 1.5 kilograms. It can therefore be comfortably handled with one hand.

The apparatus 200 housed in the housing 110 is embodied as a compact optical or optoelectronic unit, by means of which emissions of the indicator 120, or of the indicator substances 125-1, etc., can be generated and said emissions can be measured with the aid of optical and optoelectronic devices. Here, the term "emission" should be understood in the sense of an optical emission. Thus, the emission is electromagnetic radiation that emanates from, or is emitted by, the indicator substances.

Constructive and functional details of the apparatus 200 according to the embodiment or variants thereof are explained on the basis of FIGS. 1 to 4. The apparatus 200 has a plurality of radiation sources 210-1, 210-2, each of which are embodied to emit quasi-monochromatic excitation radiation. Here, the phrase "quasi-monochromatic excitation radiation" denotes excitation radiation from a relatively narrow wavelength range, for example with a spectral bandwidth of significantly less than 100 nm. By way of example, the spectral bandwidth can be of the order of approximately 10 nm or a few 10 nm. Here, the excitation is also referred to as narrow bandwidth excitation radiation. If use is made of the term "excitation wavelength", the latter relates accordingly to a relatively narrow wavelength range.

In the exemplary case, the radiation sources 210-1, 210-2 each have a light-emitting diode (LED) as an active element that emits excitation radiation. The radiation sources are connected to the control unit 115 for control and power supply purposes. The small-area, approximately punctiform radiation sources are arranged, spatially separated from one another, at various locations in a radiation area 240. The radiation area is the area in which the radiation sources lie. Like in the example of FIG. 1, the radiation area can be a plane radiation area (radiation plane) such that all radiation sources lie in a common plane. However, this is not mandatory. The radiation area may also be singly or multiply curved. The radiation area can be described in such a way that it represents a pattern of radiation sources depending on the location, i.e. a certain spatial distribution of radiation sources that are spatially separated from one another. Between the radiation sources there are lateral distances without a radiation source.

The apparatus 200 comprises an excitation beam path for imaging excitation radiation into the indicator area 130 in such a way that emissions of the indicator substances 125-1, 125-2 can be produced or excited at those locations or regions at which excitation radiation emitted by the radiation sources is imaged onto the indicator area or the indicator substance arranged there.

In the exemplary embodiment, the excitation beam path has a plurality of excitation channels, wherein each excitation channel has a first imaging system 220-1, 220-2 which defines an optical axis 222-1, 222-2 of the respective excitation channel. The excitation channels are only represented by means of lens symbols in FIG. 1; details and peculiarities are explained on the basis of the subsequent figures.

Here, the term "excitation channel" denotes the totality of all optical components that contribute to guiding excitation radiation from a primary or secondary (virtual) radiation source to the assigned indicator substance or an assigned location or region of the indicator area. An imaging system may contain a simple lens (e.g. a plano-convex or biconvex lens, a diverging lens or a ball lens), or else a lens group with two or more lenses. One or more beam shapers and/or one or more wavelength-selective elements, such as filters, for example, may also be housed in an excitation channel.

The emissions emitted by the indicator substances are guided over an emission beam path that is designed for imaging the indicator area 130 into a reception area 245 of the apparatus 200. The emission beam path is preferably designed in such a way that substantially only the regions of the indicator substances that were impinged upon by excitation radiation are captured by measurement. The reception area can be a plane area (reception plane); however, this is not mandatory. The imaging is carried out in such a way that, during measurement operation, a pattern of emissions depending on the location is present in the reception area 245. In the exemplary case, this pattern corresponds with regard to the spatial distribution of irradiated regions to the pattern which is formed by the emissions at the locations or regions in the indicator area 130 that are illuminated by excitation radiation. Consequently, the patterns are similar to one another in the geometric sense (but this is not mandatory). The imaging of the excitation radiation, the arrangement of the indicator substances and the imaging of the emissions are matched to one another.

In the exemplary case, the emission beam path has a common second imaging system 250 for all emissions, said second imaging system defining an optical axis 252 of the emission beam path. The second imaging system 250, which is only symbolized by a lens in FIG. 1, is configured in such a way that emissions can be received by all excited indicator substances on the entrance side and said emissions can be transferred to or on the reception area 240 on the exit side. The emission beam path can be described as a single emission channel which, in the case of a single common optical axis, has or provides a plurality of sub-channels for the emissions coming from differently arranged indicator substances.

An optional wavelength-selective device 260 is disposed optically downstream of the reception area 245. The wavelength-selective device has an entrance area 262, which can be impinged upon by the emission received in the reception area. The entrance area may coincide with the reception area 245 or it may have a distance from the latter. Optionally, one or more optical elements may lie between the reception area and the entrance area. An essential function of the wavelength-selective device is that of selecting or choosing a spectrum that is particularly suitable for capture and evaluation or a desired narrow spectrum from the, as a rule, relatively broad spectrum of emissions that impinge upon the reception area. Wavelength-selected emissions are present in the exit area 264 of the wavelength-selective device 260.

Receivers 270-1, 270-2 for receiving wavelength-selected emissions and for converting these emissions into electrical signals are arranged in the exit area 264. The receivers have corresponding optoelectronic components that have a signal-conducting link to the evaluation unit that is integrated into the control unit 115. The electrical signals received by the receivers are evaluated in the evaluation unit for characterizing the spectral information about the emissions that were received by the receivers.

The appliance 100 is designed, in particular, for detecting analytes in the form of explosive materials (explosives) during field operations. To this end, it is possible, in particular, to capture and evaluate temporal changes in the fluorescence intensity of the indicator substances after irradiation with excitation radiation. By way of example, quenching occurs in many cases upon contact between an analyte and an indicator substance responding thereto, i.e. there is a reduction in the fluorescence intensity emitted by the indicator substance. Then, information items about the amount of one or more searched-for target substances (analytes) and/or information about the type of detected target substances, for example, can be ascertained in the evaluation unit and output by way of the display device 117, for example.

One of the objects of the present development lies in realizing spectroscopic measurements of emissions with high sensitivity in a portable appliance that is suitable for field operations. An important measure to this end consists of designing and arranging the optical and electro-optical components that are required for generating and guiding excitation radiation and emission radiation in such a way that the optical apparatus 200 is compact enough in terms of its structure in order to be installed in a hand-held appliance. Moreover, the apparatus 200 should be robust enough to remain permanently functional, even in the case of harsh field operations (for example, during or after tremors). Moreover, high measurement sensitivity and high measuring certainty are sought after. Further measures which, individually or in combination with one another, are conducive for the suitability of the appliance for field operations are described below.

Figure 2:
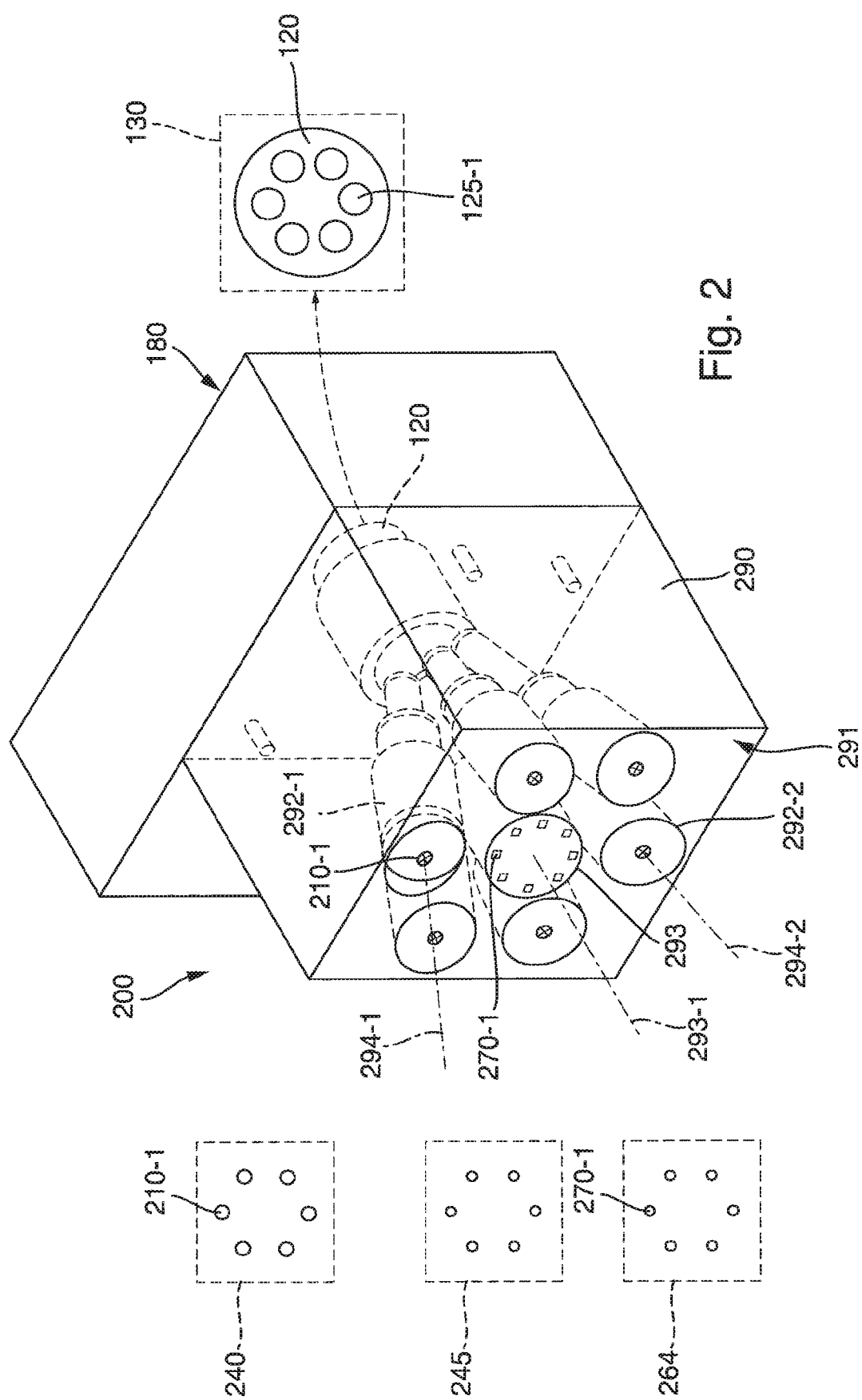
FIG. 2 shows an oblique perspective illustration of components of an optical apparatus, which are illustrated in the correct spatial arrangement together with a coupled holding apparatus for an indicator.
Figure 3:
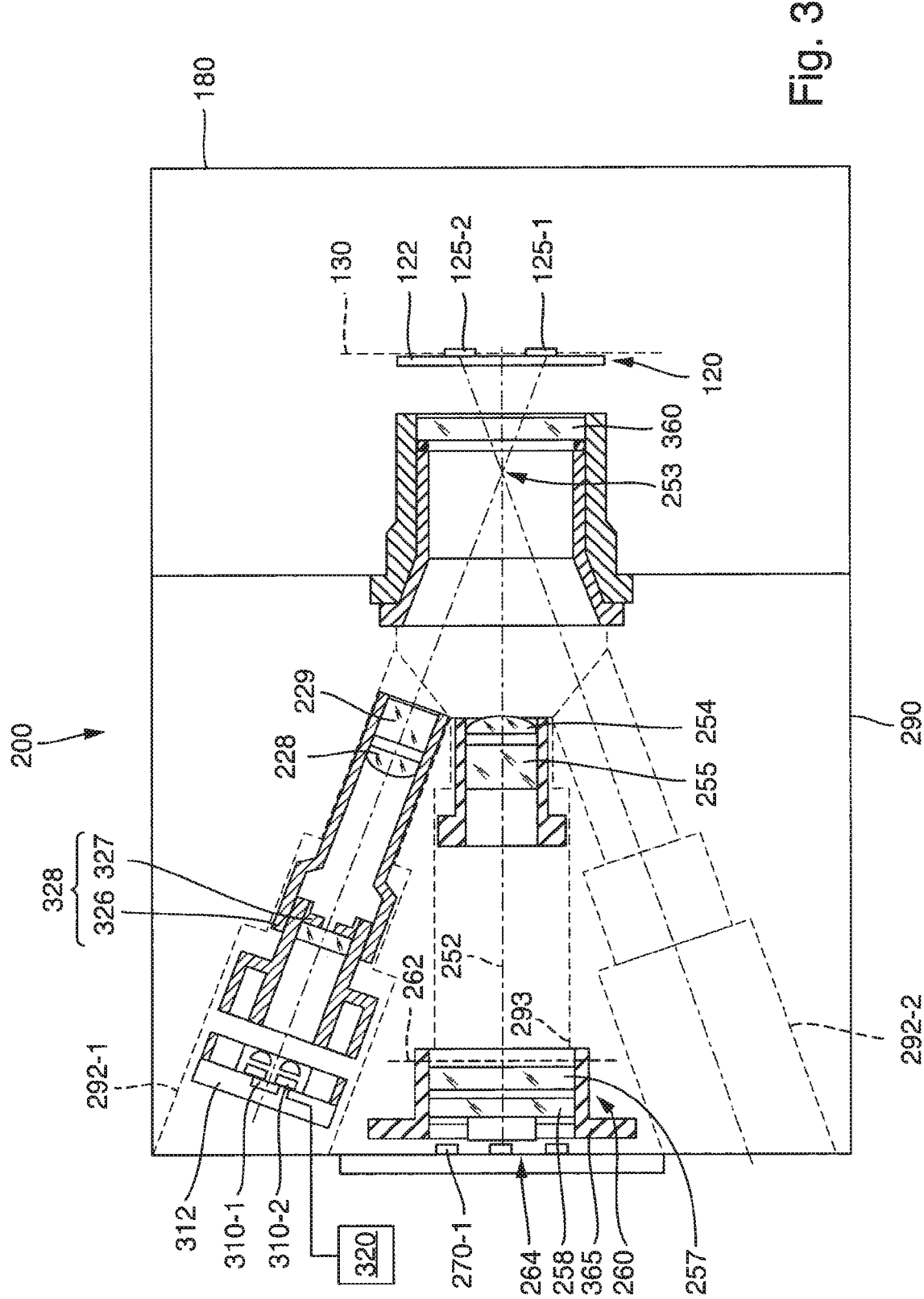
FIG. 3 shows a section through components of an optical apparatus, which is illustrated in the correct spatial arrangement together with a coupled holding apparatus for an indicator.

FIG. 2 shows, in an oblique perspective illustration, some components of the apparatus 200 which are illustrated in the correct spatial arrangement together with the coupled holding apparatus 180 (see also FIG. 3). All optical elements of the apparatus 200, i.e., in particular, all optical elements of the imaging beam path provided for influencing the radiation and all optical elements of the emission beam path provided for influencing the radiation, are integrated in a single solid cuboid component 290, which is also referred to as optics holder 290 here. In the exemplary case, the component is a monolithic block made out of a suitable torsionally rigid material, for example a metal or a ceramic. It may be an injection-molded part or a sintered part, or else a component that has been worked out of the whole by material-ablating processing. Production by way of 3D printing is also possible. The component may also be composed of a plurality of parts which are securely connected to one another, e.g. by means of screws or in an integrally bonded manner. The component 290 or the apparatus 200 can be so small that it completely fits into a cube with an edge length of ten centimeters.

A plurality of rotationally symmetric receiving channels 291-1, 292-2, 293 for receiving the optical elements of the excitation channels and of the emission channel are formed in the component 290. The longitudinal central axis of the receiving channel 293 for the optical elements of the emission channel extends perpendicular to the plane front side 291 of the component and (if the holding apparatus 180 is correctly coupled) perpendicular to the plane indicator area. The longitudinal central axes 294-1, 294-2, etc., of the receiving channels for the optical elements of the excitation beam paths extend at an angle to that of the emission channel and lie on a lateral conical face, the tapering end of which faces the holding apparatus 180. The cone angle or the angle between the longitudinal central axes of emission channel and excitation channel lies at approximately 40°, although it may also be smaller (e.g. 20° or more) or larger (e.g. 60° or less). The longitudinal central axes intersect at a distance in front of the indicator area.

The apparatus 200 has six separate excitation channels that are optically separated from one another and uniformly distributed around the emission channel, and accordingly said apparatus has six receiving channels 292-1, etc., which are uniformly distributed over the lateral conical face. These have portions of stepped diameters that become smaller toward the indicator in steps. As illustrated in an exemplary manner in FIG. 3, the optical elements of the beam paths are mounted individually or in groups in sleeve-shaped mounting elements, which may also be referred to as a tube (singular) or tubes (plural) in this case. The mounting elements fit, preferably without play, into the assigned portions of the receiving channels in the component 290 and are successively pushed into the receiving channels and affixed there during the assembly of the apparatus 200 such that the held optical elements lie with high precision at their envisaged positions along the channels.

The optical axes of the first imaging systems for the excitation radiation then coincide with the longitudinal central axes of the receiving channels 292-1, etc., of the optics holder 290 such that the excitation channels and the emission channel also form a conical arrangement, wherein the optical axes of the excitation channels are arranged on a lateral conical face that surrounds the emission channel. Then, the optical axis of the emission channel is arranged along the axis of the cone.

The optical elements are easily interchangeable by interchanging the tubes receiving said optical elements and may, if need be, be replaced by fitting tubes with other optical elements in order to re-equip the appliance for a different measurement problem.

In FIG. 2, the spatial arrangements of the radiation sources 210-1, etc., in the radiation area 240, of the indicator substances 125-1, etc., in the indicator area 120 and of the reception regions of the emission radiation in the reception area 245 are illustrated particularly vividly. The six separate radiation sources 210-1, etc., form a ring-shaped arrangement or ring-shaped matrix in the plane radiation area that lies in the vicinity of the front side 291 of the component 290. The indicator substances 125-1, etc., likewise form a ring-shaped arrangement that lies in the plane indicator area 130. After the emissions pass through the emission beam path, the emissions likewise form a ring-shaped pattern in the reception area 245, with six spatially separated regions in which emission radiation strikes the reception area. The pattern of the emissions in the reception area 245 is the integral result from the patterns of the radiation sources, of the indicator substances and of the emissions. This pattern is determined by the pattern of the radiation sources and the optics disposed downstream of the radiation sources. That is to say, the pattern of the emissions in the entrance area of the wavelength-selective device is predeterminable by the arrangement of the radiation sources, of the optical elements in the excitation beam path and the optical elements in the emission beam path.

The arrangement is such that a separate receiver 270-1, etc., is assigned to each of the indicator substances 125-1, etc. Thus, six separate receivers are provided in the exemplary case, and so the number of receivers corresponds to the number of effective radiation sources or the number of excitation channels. Interstices without receivers lie between the receivers. The receivers are separately adjustable. In the exemplary case, semiconductor-based photomultipliers, in particular on the basis of silicon (Si photomultipliers, Si-PMT), are provided as receivers. These are distinguished by high sensitivity and robustness against tremors. Alternatively, it is also possible to use e.g. conventional photomultipliers with a small installation size or photodiodes. In the arrangement, there are no two or more indicator substances which are assigned the same receiver, and so each receiver can receive at most emissions from exactly one indicator substance. As a result of this, highly selective measurements are possible.

The excitation beam path and the emission beam path are arranged in backward geometry. This means that the excitation beam path and the emission beam path are arranged on the same side of the indicator 120 or of the indicator area 130. This allows all optical components to be able to be housed within the optical apparatus 200 or within the housing 110 and allows the indicator 120 that is provided for the measurement to be able to be housed in a separate holding apparatus 180 that can be removed from the housing. The region of the holding device 180 that optionally carries gas during operation is hermetically sealed from the region of the optical beam paths by way of a protective window 360 that is transparent to the excitation radiation and the emission radiation (see FIG. 3). The easily interchangeable protective window is held by a dedicated mounting device which comprises two sleeve-shaped mounting elements that can be plugged into one another.

In principle, a problem that may occur in the case of measurements with a backward geometry is that intensity of the excitation radiation that has undergone specular reflection reaches the receiver and impairs the measurement sensitivity or the signal-to-noise ratio. Radiation that has undergone specular reflection is distinguished by this being radiation whose emergence angle from a reflective area (e.g. airindicator interface) equals the angle of incidence thereof. Special measures are taken in embodiments of the invention in order to reduce the influence on the measurement sensitivity of radiation that has undergone specular reflection.

The measurement geometry is set in such a way that radiation that has undergone specular reflection at the indicator and hence disturbs the emission measurement is practically unable to strike the reception area and consequently unable to disturb the measurement. This is achieved, firstly, by virtue of provision being made of different angles of excitation and of emission in respect of the surface normal at the indicator on the area of incidence of excitation radiation. While the excitation radiation strikes the plane indicator area at an angle, the optical axis of the emission beam path is perpendicular to the indicator area. Secondly, provision is made as a peculiarity for the optical axes of the imaging systems of the excitation beam path (first imaging systems) and of the emission beam path (second imaging systems) not to cross in the indicator area but to cross at a significant distance (e.g. of the order of one or more millimeters) in front of the indicator area, and so the points of intersection of the optical axes lie apart or are spatially separated from one another in the indicator area.

Figure 4:
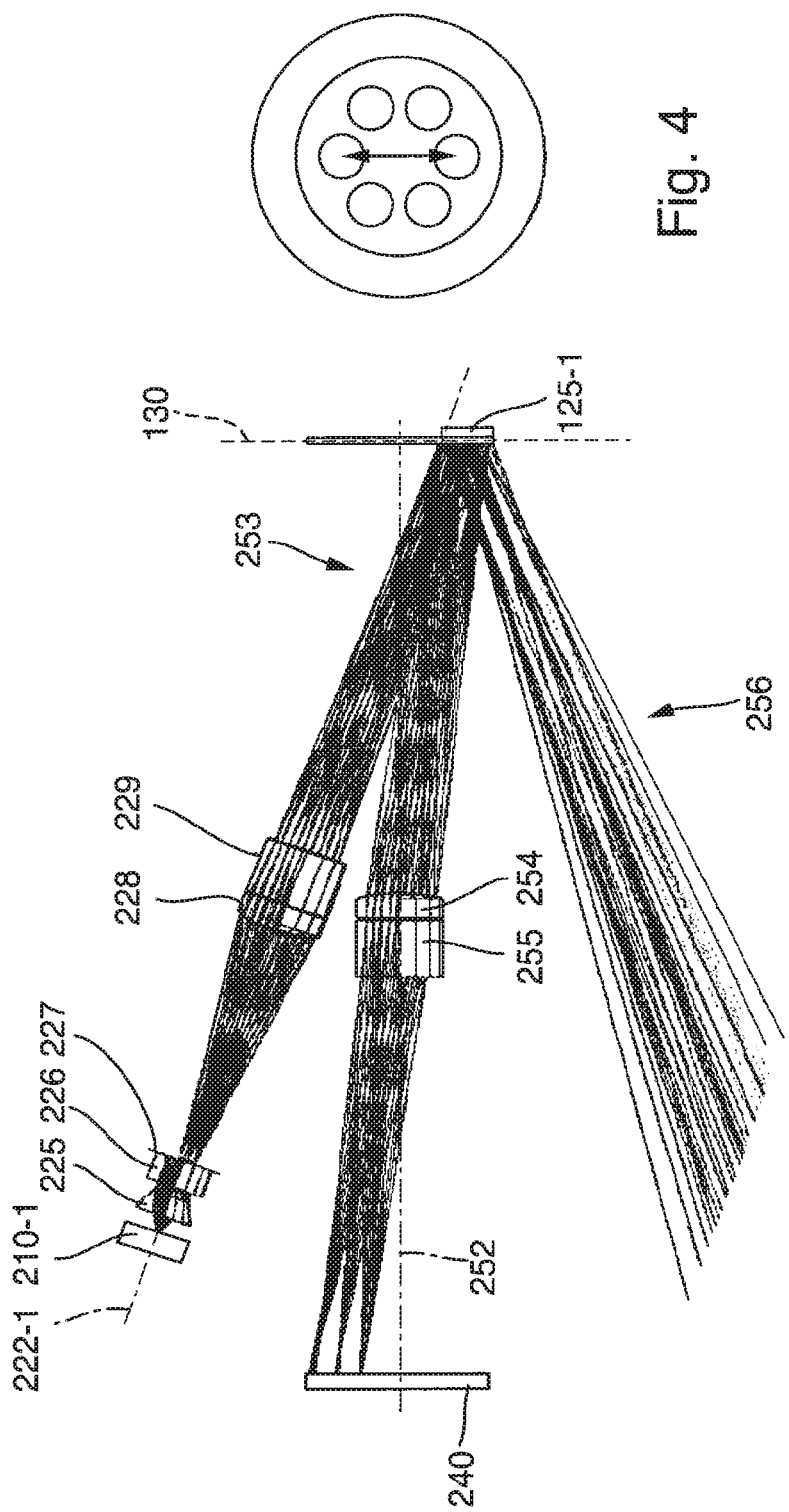
FIG. 4 shows profiles of beams in an excitation channel of the excitation beam path and in the emission beam path, wherein radiation that underwent spectral reflection at the indicator does not fall into the emission beam path.

For explanatory purposes, FIG. 4 shows an illustration in a plane that is spanned by the optical axis 252 of the emission channel and the optical axis 222-1 of a single excitation channel. The divergent excitation radiation emanating from the radiation source 210-1 is initially collimated by a converging lens 225 and subsequently strikes a beam shaper 226 in the form of a diffuser, which makes the initially non-uniform intensity profile of the radiation more uniform. The diffuser 226 has a pinhole diaphragm 227 disposed downstream thereof, said pinhole diaphragm being uniformly illuminated by the excitation radiation emerging from the diffuser. The pinhole diaphragm consequently forms a (circular) secondary effective radiation source with a very uniform intensity profile. Disposed downstream of the pinhole diaphragm at a suitable distance therefrom is a simple lens 228 in the form of a plano-convex lens, the latter being followed on the exit side thereof by an excitation filter 229. The excitation filter is designed as a band-pass filter and has the object of selecting a narrower wavelength range desired for exciting the indicator substance from the already relatively narrow bandwidth spectrum of the excitation radiation emitted by the primary radiation source 210-1. In particular, longer wavelength radiation components (e.g. longer wavelength intensity tails of LEDs) are blocked, said longer wavelength radiation components lying in that wavelength range in which fluorescence should be measured.

This narrow bandwidth excitation radiation strikes the first indicator substance 125-1 in the indicator area 130. A component of the emitted radiation (emission) provided for the evaluation reaches the receivers through the emission channel. The second imaging system, which in this case has a single optical element with refractive power, namely a plano-convex lens 254, is situated in the emission channel, said second imaging system being followed on its exit side by an emission filter 255. The emission filter is designed as a relatively broadband band-pass filter and has, inter alia, the object of blocking wavelengths from the wavelength range of the excitation radiation (in this case around approximately 370 nm). By contrast, the longer wavelength fluorescence radiation within the emission is transmitted substantially without being influenced.

It is very clear from FIG. 3 or 4 that the optical axes of the excitation beam path and of the emission beam path cross at a crossing point 253 at a distance in front of the indicator area 130, and so the excitation radiation that is emitted by the radiation source 210-1 above the emission beam path strikes the indicator area on the opposite side of the emission beam path, namely below the point of intersection of the optical axis 252 of the emission beam path. By way of example, the crossing point may lie one or more millimeters in front of the indicator area. Impinging the indicator 120 in the indicator area 130 with excitation radiation is thus effected on the optical axis of the imaging system associated with the excitation channel (said imaging system containing, inter alia, the lens 228). The excitation is effected below the optical axis of the imaging system for the emission. As a consequence, the emission emitted by the indicator substance 125-1, said emission being incident in the emission beam path, is imaged by the second imaging system (imaging system of the emission beam path) in a spatially restricted region above the optical axis 252 of the emission channel.

This is firstly advantageous for operating the apparatus 200 with a plurality of excitation channels which, in the exemplary case, are arranged symmetrically about the optical axis of the emission channel. As a result, there is a good spatial resolution in the reception area 245. Moreover, this arrangement is advantageous in that none of the excitation radiation that has undergone specular reflection at the indicator is able to reach into the emission channel. This provides the advantage that, inter alia, it is possible to use costeffective filters with less blocking or that it is possible to entirely dispense with filters. FIG. 4 vividly shows that the radiation 256 that has undergone specular reflection does not enter the aperture of the imaging system of the emission beam path (second imaging system). The excitation radiation runs along the optical axis of the imaging system of the corresponding excitation channel. By contrast, the emission radiation does not run along the optical axis of the imaging system of the emission channel but crosses said optical axis between the indicator area and the reception area. This applies to the emission radiations of all channels. They run in sub-channels within the imaging system of the emission beam path, said sub-channels in any case being present spatially separated from one another in the region of the indicator area 130 and the reception area 245.

It is possible to operate the appliance 100 or the optical apparatus 200 using only a single excitation wavelength. By way of example, the excitation wavelength may lie in the near ultraviolet range (between 350 nm and 400 nm, for example), and so the fluorescence radiation (emission radiation) that has been spectrally shifted to longer wavelengths by a red shift lies in the visible wavelength range and can be detected by appropriate receivers. It is also possible for the indicator substances to be identical to one another from a chemical-physical point of view, and so the apparatus could carry out six nominally identical measurements at the same time.

However, it is also possible to use two or more indicator substances that differ from a chemical-physical point of view. By way of example, different indicator substances could be optimized for different classes or groups of explosive materials. By way of example, the apparatus could be used in such a way that three different types of indicator substance lie in two of the used positions within the indicator area in each case. These may all be irradiated with the same excitation wavelength. However, it is also possible to use different excitation wavelengths that have been matched to the different indicator substances.

The apparatus 200 may be operated in such a way that all radiation sources are switched to be active at the same time. The configuration ensures that the emissions in the entrance area of the wavelength-selective device are separated from one another in terms of location or spatially separated from one another and hence decoupled such that the emissions are resolvable without mutual superposition of emissions. The configuration automatically ensures that the impingement of the entrance area of the wavelength-selective device with a plurality of emissions does not occur simultaneously at the same location. A local separation is provided for the receivers, and so there cannot be a superposition of various spectra.

In the case of the arrangement, it is also possible to operate, at least in part, with different excitation wavelengths in the different excitation channels. Thus, for example, two or more types of radiation sources can be used, said radiation sources each producing excitation radiation in different wavelength ranges. By way of example, it is possible to use three different wavelength ranges, wherein the same excitation wavelength is then used in respectively two of the excitation channels.

FIG. 3 is used to explain an exemplary embodiment in which it is possible to selectively operate a single excitation channel with two different excitation wavelengths. Two radiation sources 310-1, 310-2 in the form of LEDs with different excitation wavelengths are attached to a carrier 312. The radiation sources are connected to a clock generator or clock 320, which may be a functional constituent part of the control device 115 of the appliance 100. Using the clock generator, it is possible to switch the light sources separately from one another, in particular alternately, and so only one excitation wavelength is coupled into the excitation channel in each case.

The divergent radiation emitted by the radiation sources impinges upon a beam shaper 326 in the form of a diffuser. A pinhole diaphragm 327 is disposed downstream of the latter, the hole of said pinhole diaphragm being seated centrally in relation to the optical axis. The arrangement is configured in such a way that, independently of which of the radiation sources 310-1, 310-2 is activated, the hole of the pinhole diaphragm is illuminated uniformly with the radiation of the activated radiation source. Thus, a secondary radiation source with the excitation wavelength corresponding to the wavelength of the activated primary radiation source is formed in the region of the hole.

Hence, the downstream first imaging system (with a single plano-convex lens in this case) "sees" only a single location (hole of the pinhole diaphragm) for a plurality of primary radiation sources. Consequently, the diffuser with a downstream pinhole diaphragm satisfies the function of a radiation source merging device or a radiation merging device 328. The virtual or secondary radiation source, formed in the region of the pinhole diaphragm, is able to emit different excitation wavelengths, depending on which radiation source is switched to be active by the clock generator. Corresponding arrangements with three or more primary radiation sources are likewise possible. Such a multiplication of effective radiation sources can be provided in a single excitation channel, in a plurality of excitation channels or in all excitation channels.

As already mentioned, the wavelength-selective device 260 has, inter alia, the function of selecting a narrower wavelength range or a plurality of different narrower wavelength ranges from the emission radiation striking the reception area 245, the intensity of said narrower wavelength range or ranges then being able to be measured by means of the receivers. In the example of FIG. 3, the wavelength-selective device 260 has a band-pass filter arrangement which passes the same wavelength range for all receivers and which blocks radiation components that are not wanted for the evaluation. It is also possible to design a wavelength-selective device in such a way that different wavelength ranges for the reception and the evaluation are passed for different receivers or different groups of receivers. Consequently, it is then possible, if necessary, to simultaneously measure and evaluate a plurality of relatively narrow wavelength ranges in a broader fluorescence spectrum.

In the illustrated example of FIG. 3, the following elements are arranged or arrangeable in the emission channel: a plano-convex lens 254, an optional emission filter 255 (common filter for all receivers), a short-pass filter 257 as a common filter for all receivers, a long-pass filter 258 as a common filter for all receivers. Reference sign 365 denotes a holder for band-pass filters, for example, which may be provided separately for each receiver. In the example, this holder is not occupied. Where necessary, the combination of a short-pass filter 257 and long-pass filter 258 can assume the function of an emission filter, and so it is possible to dispense with a separate emission filter.

In the exemplary embodiment, it is possible, in principle, to measure and evaluate up to six different wavelength ranges together, said wavelength ranges being spectrally separated from one another, if this is desired. As is clear from FIG. 3, the filter elements of the wavelength-selective device are mounted in a dedicated mounting device 365 which is easily interchangeable after removing the carrier for the receivers 270-1, etc. Consequently, it is possible to select different spectral ranges for the application while using the same receivers purely by interchanging the wavelength-selective device. Movable devices, such as e.g. a filter wheel, are not required.

There are also exemplary embodiments that make do without a wavelength-selective device, and so the emissions in the reception area can reach the receivers without further spectral restriction. In this case, the active areas of the receivers can be arranged directly in the reception area 245 or in the vicinity thereof.

If a wavelength-selective device is provided, the slit of a grating monochromator may be arranged in the entrance plane of said wavelength-selective device, for example. It is also possible for an opening for a defined passage of the emission into a filter monochromator with separate band-pass filters or with a graduated filter to be localized in the entrance area. Other optical elements may be arranged between the reception area and the entrance area. By way of example, provision may be made there of an imaging system having an imaging element or a plurality of imaging elements in order to realize imaging of the emissions of the reception area onto the entrance area.

The concept proposed here offers the option of measuring at a larger number of excitation and emission wavelengths if necessary. As a result of this, the information content of the measurement values may possibly be increased. Since the number of wavelengths and the spectral resolution can be restricted in comparison with fully scanning spectrometers on account of their use of narrowband light sources, it is possible to provide apparatuses with a small installation size that can be housed in an appliance that is suitable for field operations.

In some exemplary embodiments, use is made of three to nine excitation wavelengths in the ultrawave spectral range (300 nm to 400 nm) and of three to nine emission wavelengths in the visible spectral range (400 nm to 700 nm). It was recognized that a complete wavelength scan is not required for the applications representing the main focus. Instead, narrow bandwidth wavelength ranges, which may originate from a broad spectrum, are sufficient.

The indicator may have two or more different indicator substances, as a result of which it is possible to increase the selectivity and reduce disturbances. If use is made of a plurality of different indicator substances (for example two, three, four or five different indicator substances), it may be the case that changes in the emission can be characterized better and, as a result, the signal interpretation can become more accurate. This may lead to a reduction of inaccuracies and to an improvement of the measuring certainty in the field of identifying explosive materials and other substances that are relevant to health and the environment.

Below, numerous further examples are explained, each of which being equipped with an optional wavelength-selective device between reception area and the receivers (one or more).

The excitation beam path of the examples only has a single excitation channel in each case, which is used, either simultaneously or successively in time, by the radiation of all radiation sources (one or more). Preferably, the exemplary embodiments use more than one excitation wavelength, for example two or three to nine spectrally different excitation wavelengths. In the schematic illustrations, the same reference signs are used in each case for the same or similar components or features.

Figure 5:
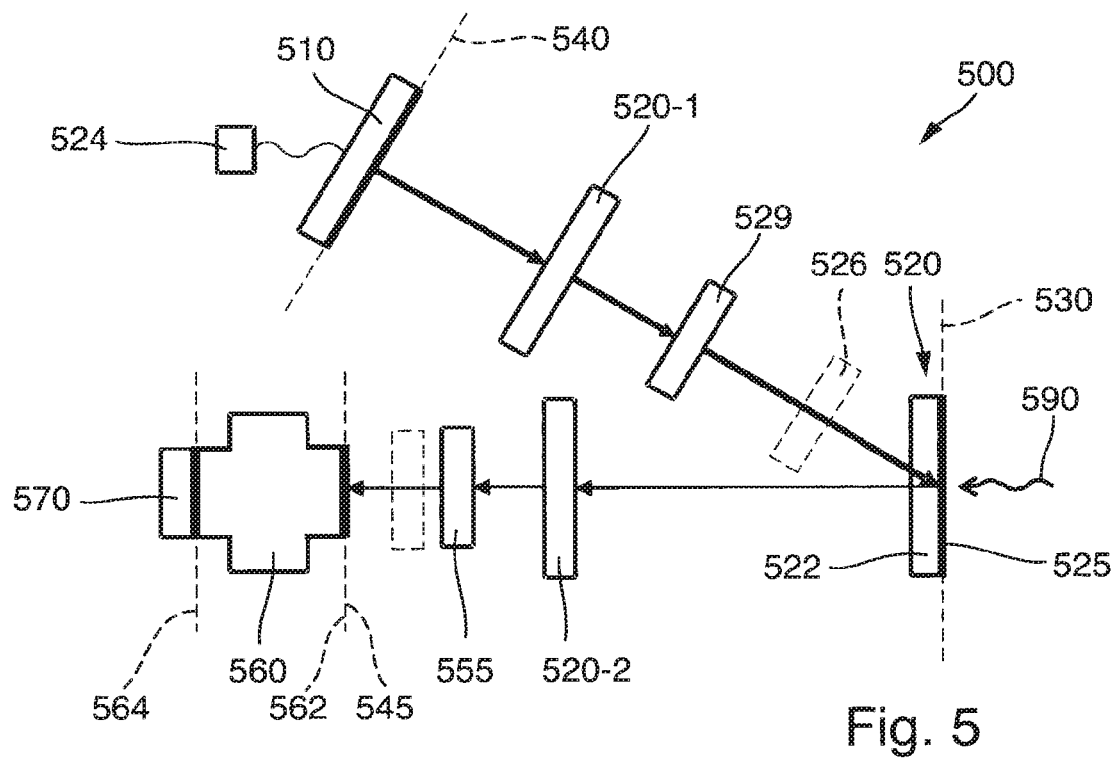
FIG. 5 schematically shows some components of an apparatus for generating and detecting optical emissions of indicators according to an exemplary embodiment having only one excitation channel and one emission channel.

FIG. 5 shows a schematic illustration of an exemplary embodiment of an apparatus 500 for generating and measuring emissions of an indicator 520 having a carrier 522, on which indicator substances 525 (one or more) are applied as a thin layer, said indicator substances being able to be impinged upon by analytes 590. The holding apparatus that carries the indicator has not been depicted. In the primed assembled apparatus or primed assembled appliance, the indicator substances are situated in the indicator area 530, which may be curved but is a plane (indicator plane) in the exemplary case. Radiation sources 510 (one or more) are situated in the (plane) radiation area 540. These each have a narrow bandwidth and emit quasi-monochromatic excitation radiation upon activation. An optional clock 524 serves to activate and deactivate some or all of the radiation sources, and so a pattern of radiation sources depending on location and/or depending on time can be produced in the radiation area.

The excitation beam path for imaging excitation radiation into the indicator area 530 has only a single excitation channel in the exemplary case, said single excitation channel extending at an angle in relation to the indicator area and comprising a first imaging system 520-1 that defines an optical axis of the excitation channel. The excitation channel provides a plurality of sub-channels for excitation radiation propagating to the indicator. The first imaging system may have a single lens (simple lens), but optionally also a plurality of optical elements with refractive power. As a rule, an excitation filter 529, and also an optional first beam shaper 526 in some embodiments, is situated in the imaging beam path.

An emission beam path serves for imaging the indicator area 530 into a reception area 545 which, in the exemplary case, is a plane area (reception plane). The emission beam path for imaging emission radiation has only a single emission channel. It provides a plurality of sub-channels for the emissions propagating from the indicator to the reception area. The emission beam path comprises a second imaging system 520-2, the optical axis of which is perpendicular to the plane indicator area 530 in the exemplary case. In the example of FIG. 5, the emission beam path still contains an emission filter 555, which may be dispensed with in other variants. Following the reception plane 545 in the radiation direction is a wavelength-selective device 560, the entrance area 562 of which coincides with the reception area 545 in FIG. 5. Receivers 570 (one or more) for the emission are arranged in the exit area 564 of the wavelength-selective device, or in the vicinity thereof. The receivers serve for receiving emissions from the reception area 545 and for converting the received emissions into electrical signals. By way of example, the receivers can be configured as photomultipliers, in particular as silicon photomultipliers.

Like in the embodiments described above, the optical elements of the excitation beam path and of the emission beam path may be integrated in a common optics holder. The realization (with receiving channels for optical elements in a single-part or multi-part block) may be similar as in the preceding examples.

The apparatus 500 is designed to capture emissions in the case of a larger number of excitation wavelengths and emission wavelengths. Using this, it is possible to increase the information content over variants with only a single excitation wavelength in certain applications. However, the number of usable wavelengths and the spectral resolution is deliberately restricted by the apparatus in comparison with scanning spectrometers such that the apparatus 500 can be used in an appliance that is suitable for field operations for detecting explosive materials and/or other substances that are a risk to the environment and health.

In the exemplary embodiments explained below, use is made of three to nine excitation wavelengths in the ultraviolet spectral range (300 nm to 400 nm) and of three to nine emission wavelengths in the visible spectral range (400 nm to 700 nm). A complete wavelength scan is neither required nor structurally envisaged. Sufficient measurement accuracy is obtained in the apparatus by using narrow bandwidth wavelength ranges from a broader spectrum.

The indicator 520 may have a plurality of indicator substances and is interchangeable, as a result of which it is possible to increase the selectivity and reduce disturbances. What this can achieve is that the changes in the emissions are characterized better and the signal interpretation is more accurate as a result thereof, which may be advantageous in some classes of analytes. In comparison with solutions of the prior art, this can be used to reduce inaccuracies and improve the measuring certainty in the field of identifying explosive materials and other substances that are relevant to health and the environment.

The radiation sources 510 in the radiation area 540 are responsible for the decoupled emission of excitation radiation, with this decoupling being able to relate to both the location and the time. By way of example, the excitation radiation may be emitted at one location at different times or at different locations at one time or else at different locations at different times. In the exemplary case, the narrow bandwidth excitation radiation is produced by spectral emitters (LEDs), but it may also be produced with the aid of wavelength-selective devices, such as gratings or filters, for example.

Each location in the radiation area 540 occupied by a radiation source 510 represents a certain excitation wavelength. Consequently, the radiation area represents a pattern of radiation sources depending on location. With the aid of the clock 524, the radiation sources may also operate in flash operation, i.e. they are clockable (activatable and deactivatable) in time in a defined manner by way of the clock generator 524. Consequently, the radiation area represents not only a pattern of radiation sources 510 depending on location but also a pattern of radiation sources 510 depending on time. The radiation area may have a plane or curved embodiment. In the exemplary case, this is a radiation plane.

Figure 6:
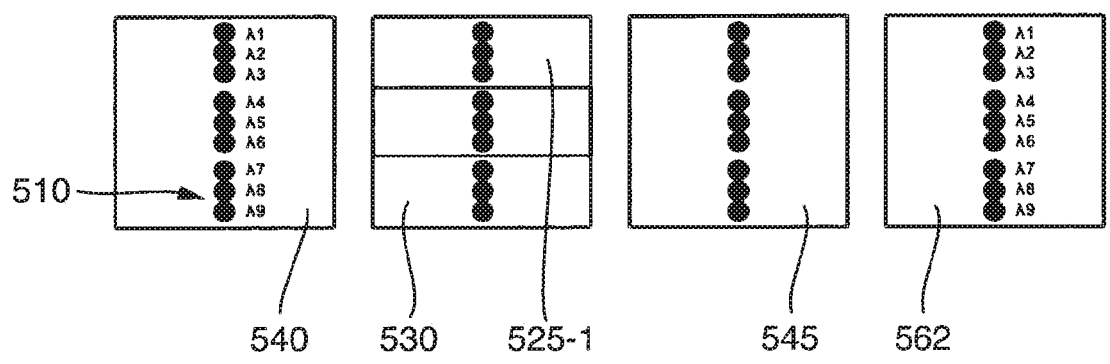

FIG. 6 presents, for one exemplary embodiment, the conditions in the radiation area 540, the indicator area 530, the reception area 545 and the entrance area 562 of the wavelength-selective device 560.

In the exemplary case, the indicator substantially consists of a carrier on which a plurality of indicator substances 525-1 to 525-3 are applied in the form of stripes situated next to one another. Consequently, the indicator area represents a pattern of (three) indicator substances depending on location. The radiation sources are imageable into the indicator area by way of suitable measures, namely by way of the design of the imaging beam path. In this way, the indicator substances are excited to emit by way of the excitation radiation. The emission of the indicator substances is produced at exactly those locations or small-area regions where the excitation radiation is imaged onto the indicator area. Consequently, the indicator area represents not only a pattern of indicator substances depending on location but also a pattern of emissions depending on time. Here, the two patterns can be matched to one another in such a way that, firstly, the indicator substances 525-1, etc., are respectively excited to emit by radiation sources of different wavelengths. Secondly, the location and time dependence of the emissions is set in such a way that, using this, it is possible to take account of the properties of the wavelength-selective device (for example the type of the entrance area and the exit area of the wavelength-selective device 560 and the type of the receivers 570). The configuration is such that the spectrally resolved emissions can be measured without mutual superposition at the receivers.

The patterns of the radiation sources and of the indicator substances are adaptable to the flow conditions and to the geometry of the impingement of the indicator by the analyte 590, and vice versa. As already presented, the impingement can be effected in the form of a guided air flow, for example. As described in the other exemplary embodiments, the indicator 520 is mechanically coupled to the apparatus 500 with the aid of the holding apparatus in such a way that the indicator substances 525-1, etc., are positioned in an exact and defined manner in the indicator area 530. The indicator is easily interchangeable by way of this holding apparatus.

The emissions emanating from the indicator substances are imaged in the reception area in a defined manner by way of suitable measures, namely the design of the emission beam path. Consequently, the reception area 545 represents a pattern of emissions depending on location and time. The emissions can reach the entrance plane of the wavelength-selective device directly from the reception plane or they may be influenced by interposed optical means. There is a spectral resolution of all emissions with the aid of the wavelength-selective device 560, said emissions then being directed to defined locations of the exit area of the wavelength-selective device. The receivers 570 (one or more) are situated there. What can be achieved by impinging the exit area with spectrally resolved emissions at defined locations and/or at defined times (by way of the temporal clock of the radiation sources) is that the spectrally selected emissions from each location of the indicator area can be received separately and without mutual superposition by the receivers (one or more) and can be converted into signals.

The clocking with the aid of the clock 524 can be carried out in different ways. By way of example, all radiation sources may be clocked in succession with a time offset (i.e. serially) or else a part thereof may also be clocked simultaneously. The configuration is set up in such a way that the condition that the impingement of the receiver or receivers 570 with a plurality of emissions cannot be effected simultaneously at the same location is always observed. A spatial and/or temporal separation may be provided for the receivers so that there is no superposition of different spectra. By way of example, a plurality of receivers may be arranged, with distance from one another, in a one-dimensional or two-dimensional receiver array according to a certain pattern in the exit area.

The entire apparatus 500 has a modular construction. Thus, it is possible, for example, to interchange radiation sources 510, indicators 520 and/or receivers 570 without intervention in the excitation beam path and/or emission beam path. The spectral bandwidths, for example, of the excitation filter and/or of the emission filter and/or of the wavelength-selective device can be modified by interchanging these components. The apparatus 500 is also suitable for being equipped with only a single indicator with a single indicator substance and with only a single radiation source. The apparatus 500 makes do without movable parts. This contributes to the robustness of the apparatus and to the suitability for use in field operations. Furthermore, no geometric or physical beam splitter is required or provided. This is conducive, inter alia, to the measurement sensitivity.

In the apparatus 500, the pattern of the emissions in the entrance area 562 of the wavelength-selective device is predeterminable by the type and, optionally, the distribution of radiation sources and the imaging optical systems in the excitation beam path and emission beam path. In the exemplary case, the radiation area 540 is localized outside of the single focal length of the first imaging system 520-1 and the indicator area 530 localized outside of the single focal length of the second imaging system 520-2. What this can achieve is that the first imaging system images the radiation area into the indicator area. Then, the pattern of the radiation sources 510 is retrieved on the indicator area and produces a corresponding pattern of emissions. The second imaging system 520-2 images the indicator area in the reception area in backward fashion. Then, the pattern of the emissions is retrieved in the reception area 545. The planes are spaced apart at a distance in each case.

On account of this arrangement in backward geometry, the indicator 520 can be constructed particularly easily as a separate element and can be embodied to be hermetically sealable from the optical apparatus 500. This may be advantageous, inter alia, if the indicator needs to be interchanged without damaging or dirtying optical elements in the process. Moreover, this also renders it possible to expose the indicator to a defined heat treatment for the purposes of adsorption and desorption of analytes, without interfering with the measurement process.

In the apparatus 500, the radiation area 540 is adjustable along and/or transverse to the optical axis of the first imaging system 520-1. The indicator area 530 is adjustable along and/or transverse to the optical axes of the first and second imaging systems. An adjustability along and/or transverse to an optical axis in this case means that it is possible to set the distance between the radiation area and the imaging system and the distance and the angle between the radiation area and the optical axis of the first imaging element. The same applies analogously to the indicator area. Consequently, the measurement geometry can be set in such a way that radiation that has undergone specular reflection at the indicator 520 and consequently interferes with the emission measurement is unable to strike the reception area and therefore unable to reach into the wavelength-selective device 560 either (see FIG. 4).

Moreover, what can be achieved is that different patterns of the emission can be realized on the indicator area. Thus, for example, the size (diameter) of the individual elements of the pattern can be set or adjusted by defined distances of the radiation area from the first imaging system 520-1. Then, it may be advantageous if the size of the individual elements of the emission (spots corresponding to the imaging of the individual radiation sources in the indicator area) should be adapted to the areal extent of the individual indicator substances that are applied to the carrier.

The excitation filter 529 and the emission filter 555 may have the same functions as already described in conjunction with the first exemplary embodiment. Using these components, it is possible to carry out emission measurements with a high signal-to-noise ratio.

The wavelength-selective device 560 can be a filter monochromator with one or more edge filters. It would also be possible to use a grating monochromator as a wavelength-selective device. The entrance plane is often embodied in the form of a slit in the case of a grating monochromator, the emissions having to be input coupled by way of said slit. In the exemplary case of FIG. 6, the radiation sources 510 are arranged, in accordance with FIG. 6A, in the form of a straight row or column. These radiation sources are imaged into the indicator area 530 according to FIG. 6B by way of the first imaging system 520-1. In the exemplary case, three indicator substances lie in the indicator area, said indicator substances being applied horizontally on the carrier in the form of stripes that lie next to one another. Each indicator substance is impinged upon by excitation radiation at three different wavelengths λi. A pattern of excitation radiation, which is embodied as a column (one-dimensional matrix), arises. A corresponding pattern (one-dimensional matrix) of emissions in the reception plane 545 (FIG. 6C) arises as a result of the imaging via the emission beam path. These are the images of the regions of the indicator substances that are illuminated in the indicator area. The arrangement is adjusted in such a way that all the emissions of this row enter the entrance slit of the grating monochromator. The imaging of the emissions in the entrance area are arranged in three groups λ1 to λ3, λ4 to λ6 and λ7 to λ9 according to FIG. 6C or 6D. Each group represents the emissions of an indicator substance at three wavelengths of the excitation radiation.

By way of example, the size of the illuminated "spots" in the indicator area may lie in the range from one to two millimeters, but may also substantially deviate therefrom. The temporal clocking of the radiation sources with the clock generator is configured in such a way that the radiation sources are actuated successively in time in each group. Consequently, there is no superposition of different spectrally resolved emissions on an assigned receiver. What can be achieved by the configuration is that each indicator substance can be measured in the case of three different excitation wavelengths and, depending on the type of monochromator, in the case of at least three emission wavelengths. Hence, there is much information content for the evaluation.

Figure 7A:
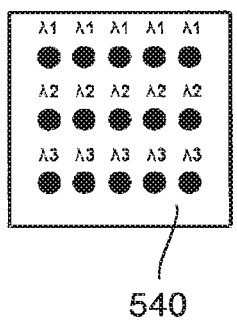
Figure 7B:
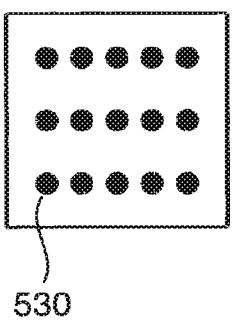
Figure 7C:
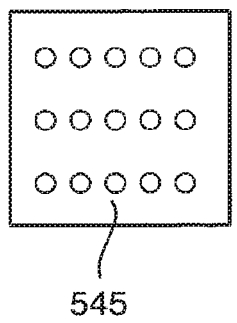
Figure 7D:
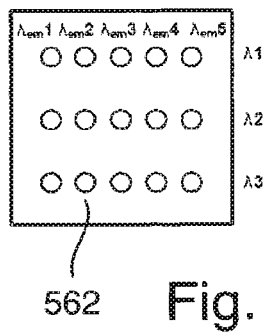
Figure 8A:
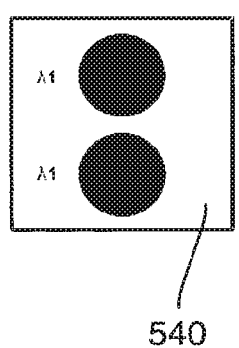
Figure 8B:
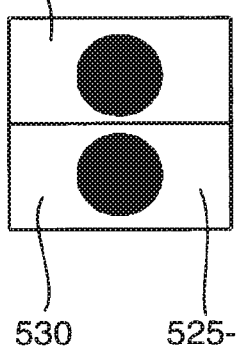
Figure 8C:
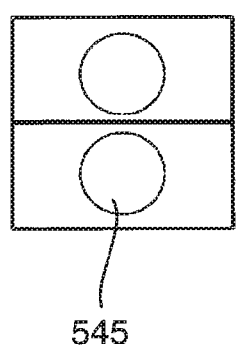
Figure 8D:
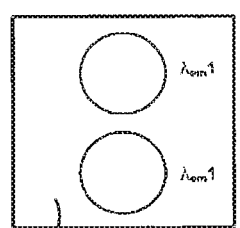
Figure 9A:
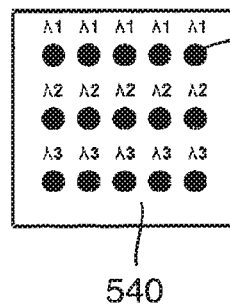
Figure 9B:
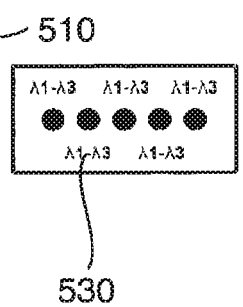
Figure 9C:
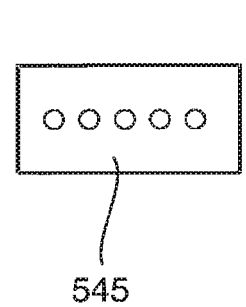
Figure 9D:
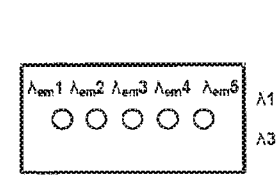

Other spatial and/or temporal patterns of the arrangement of radiation sources, emissions and/or indicator substances and combinations thereof are also possible. In the schematic example of FIG. 7, the associated apparatus is designed in such a way that a filter monochromator with one or more spectrally selective filters is used as a wavelength-selective element. According to FIG. 7A, the radiation sources are arranged in the form of a rectangular matrix with a total of 15 separately usable radiation sources. Here, the radiation sources in the same line respectively have the same excitation wavelengths (λ1, λ2 or λ3) but the radiation sources in the same column have different excitation wavelengths. For reasons of simplicity, three different excitation wavelengths λ1 to λ3 are used here. Imaging into the indicator area leads to the illuminated spots likewise being present as a two-dimensional 3×5 matrix (FIG. 7B). Here, the indicator only carries a single indicator substance which is irradiated by a total of three different excitation wavelengths at a total of 15 locations or regions that lie spatially apart from one another. However, the area of the applied indicator substance may also substantially correspond to the respectively irradiated area only. By imaging in the emission beam path, the reception plane 545 is also present with a pattern of imaged emissions in the form of a 3×5 matrix. The wavelength-selective device has an array of filters, wherein the pattern of the filters corresponds to the pattern of the imaged emissions. By way of example, the filters can transmit different wavelengths in the same line and the filters can transmit the same wavelengths in the same column. The wavelengths of the filters are matched to the wavelengths of the emissions. Since the wavelength range of the emissions usually lies at longer wavelengths than the wavelength range of the excitation radiation, the wavelengths of the filters $\lambda_{em1}$ to $\lambda_{em5}$ are greater than the wavelengths λ1 to λ3 of the excitation radiation. Thus, for example, the excitation wavelengths λ1 to λ3 may be arranged in the range from 350 nm to 400 nm and the emission wavelengths $\lambda_{em1}$ to $\lambda_{em5}$ may be arranged in the range from 450 nm to 650 nm.

Once again, a receiver array with a total of 15 receivers is arranged in the exit area of the wavelength-selective device. Said receivers are locally distributed in such a way that the pattern of the receiver elements corresponds to the pattern of the imaged emissions or to the pattern of the filters. Consequently, exactly one filter is assigned to each receiver element. Thus, in the exemplary case, the receiver consists of three lines lying one above the other, which each contain five receiver elements (3×5 receiver array). The spectral resolution of the emissions in this arrangement is effected in the line direction. Each line represents a defined excitation wavelength, and so spectrally resolved emissions emerge at five different emission wavelengths and three different excitation wavelengths. In this arrangement, temporal decoupling of the radiation sources is not required; all radiation sources can be actuated simultaneously by the clock generator.

If only a single receiver is intended to be used in place of a receiver array having a plurality of separate receivers, it is possible to clock the radiation sources in succession. The indicator may also have a plurality of indicator substances.

FIG. 8 is used to explain an exemplary embodiment in which exactly two different indicator substances 525-1 and 525-2 are provided in the indicator area 530 and in which the wavelength-selective device is designed with one or more spectrally selective filters. Use is made of two radiation sources 510 which, according to FIG. 8A, are arranged with distance from one another in one column. A corresponding arrangement emerges in the indicator area (FIG. 8B), in which exactly two different indicator substances are applied. As a result of the imaging in the emission beam path, the pattern of two emissions lying at a distance from one another, shown in FIG. 8C, arises in the reception area or in the entrance area of the wavelength-selective device. Filtering is effected in the same wavelength range for both emissions, for the purposes of which use can be made of a common filter or a filter array. The assigned receiver array consists of two separate receiver elements. The radiation sources can be actuated simultaneously by way of the clock generator. Clocking is also possible. Thus, in principle, a single receiver can be used for both emissions if, in that case, the radiation sources are clocked in succession such that temporal decoupling is realized.

In principle, it is also possible still to use non-imaging optics or a beam former, which may likewise be adjustable, in the excitation beam path and/or in the emission beam path in addition to an imaging system. In the exemplary case of FIG. 9, a beam shaper is used in the associated apparatus 500 in order to obtain an arrangement of the emissions in only a single row (one-dimensional matrix) in the region of the reception area 545 when using a two-dimensional 3×5 matrix of 15 radiation sources 510 in the radiation area 540. Thus, an image conversion is integrated by means of a beam shaper. In the exemplary case, a beam shaper 526 in the form of a cylindrical lens is introduced into the excitation beam path between the first imaging system 520-1 and the indicator area 530. As a result, a two-dimensional matrix arrangement of radiation sources 510 can be imaged into a one-dimensional matrix, i.e. a row of illuminated spots. Accordingly, the receivers of a receiver array may then also be arranged in one row.

For the different excitation wavelengths λ1 to λ3, the radiation sources can be actuated in succession by the clock generator. Radiation sources with the same excitation wavelength (i.e. radiation sources lying next to one another in a row) can be clocked simultaneously.

To the extent that a beam shaper is desired for redistributing the arrangement of excitation radiation and/or emissions, it is also possible to use an optical fiber bundle as a beam shaper. In the example of FIG. 10, such beam shaping is effected between the reception area 545 and the entrance area 562, following said reception area in the beam path, of a wavelength-selective device that lies behind the reception area with an optical and spatial distance. A total of nine radiation sources with a total of nine excitation wavelengths are used in the radiation area 540. The radiation sources are arranged in the form of a two-dimensional 3×3 matrix. The indicator substances are present in the form of three separate stripes of different indicator substances. These are respectively excited successively in time by three of the wavelengths. Consequently, a pattern of emissions depending on location, likewise in the form of a 3×3 matrix, arises in the reception area 545. The beam shaping between the reception area 545 and the entrance area 562 of the wavelength-selective device 560 is then selected in such a way that the nine emissions are arranged in three groups with in each case three different wavelengths in a single row or column (FIG. 10D). A grating monochromator or a filter monochromator can be used as a wavelength-selective device in this configuration.

FIG. 11 is used to explain a variant in which a beam shaper or non-imaging optics is/are arranged both in the excitation beam path (between radiation area 540 and indicator area 530) and in the emission beam path (between indicator area 530 and reception plane 545). By way of example, it is possible to use a cylindrical lens as a beam shaper in the excitation beam path and in the emission beam path. The radiation sources (FIG. 11A) are, once again, arranged in the form of a 5×3 matrix, with use being made of three excitation wavelengths. By way of the beam shaper in the excitation beam path, there is imaging onto the indicator area 530, in which five different indicator substances are situated in the form of stripes that lie next to one another. The imaging is effected in such a way that each of the indicator substances can be irradiated by each of the three excitation wavelengths in a temporally separated fashion. The radiation sources are imaged in the form of a single row onto the indicator substances. The beam shaper in the form of a cylindrical lens within the emission beam path is designed in such a way that the emissions of the indicator area are imaged onto a single point (spot with a finite area) in the reception area 545. The second imaging system in this case consists of a plurality of lenses, namely a lens array that is embodied as a splitter, wherein a lens that collimates the diverging radiation of the emission is assigned to each of the indicator substances in the indicator area and hence to each emission. Consequently, parallel radiation at five different locations is supplied as a line to the downstream cylindrical lens. The cylindrical lens is configured in such a way that it changes the direction of the emissions to the left and to the right of the central emission, but does not change the direction of the central emission. The cylindrical lenses of excitation beam path and emission beam path are rotated by 90° in relation to one another.

By way of example, a grating monochromator, the entrance slit of which is embodied in a punctiform or circular manner with a defined area, may be used as a wavelength-selective device. By way of this aperture, the emission in the entrance area 562 always couples into the wavelength-selective device at the same location. In the grating monochromator there is a spectral resolution of the emission, which has a line-shaped embodiment. A line-shaped receiver array is arranged in the exit area of the grating monochromator, the receivers of said receiver array being adapted to the spectral resolution of the emission.

In this case, for the various excitation wavelengths λ1 to λ3, the radiation sources are actuated in succession by the clock generator in such a way that, in each case, only a single indicator substance in the indicator area is impinged upon by excitation radiation at only a single wavelength. What this can achieve is that the spectrally resolved emissions separately reach into the wavelength-selective device without superposing in a bothersome manner, and can be measured by way of the receivers.

A further variant is explained on the basis of FIG. 12. Firstly, the emission of the indicators can be produced by excitation radiation (fluorescence, phosphorescence). Secondly, however, the emission may also be caused by chemical reactions (chemiluminescence). Therefore, in this variant, (at least) one indicator substance 525-3 that is capable of chemiluminescence is also arranged in the indicator area 530 in addition to two indicator substances 525-1, 525-2 that are capable of fluorescence. The pattern of the emissions in the entrance area of the wavelength-selective device is predeterminable here by the radiation sources 510, imaging optics and by the arrangement of the chemiluminescent indicator substances in the indicator area. The emission of the chemiluminescent substances is produced by a chemical reaction between the analytes and the indicator substances. Consequently, excitation radiation is not required for this form of luminescence. One or more indicator substances may be applied on the carrier in a defined manner. Here, this region lies outside of the region that can be impinged upon by excitation radiation of the radiation sources for the emission in the form of fluorescence. Hence, the emissions produced by analytes can be imaged at locations in the reception plane that are free from emissions produced by excitation radiation. There are no bothersome superpositions of the various emissions. Consequently, it is possible to use in a common optical unit different indicators whose emissions are producible firstly by excitation radiation and secondly by analytes by a chemical reaction. Consequently, the selectivity is increased and disturbances are reduced. However, it is also possible to only use chemiluminescent indicator substances in the optical unit. Then, there is no need to arrange or use radiation sources for excitation radiation.

The condition that the impingement of the entrance area with a plurality of emissions (at the same or different emission wavelengths) does not occur simultaneously at the same location is always maintained in each of the cases that are illustrated in an exemplary manner. Imaging systems, beam shapers and/or clocks, inter alia, are suitably arranged and operated for impinging the reception plane and/or an entrance plane of a wavelength-selective device with emissions at one location or at different locations and/or at different times.

Consequently, the disclosure of this application describes, inter alia, an apparatus for generating and measuring the emission of an indicator that has a carrier and at least one indicator substance that can be impinged upon by analytes (590), having at least one radiation source for excitation radiation and at least one receiver for measuring the emission, wherein the apparatus is characterized in that one or more radiation sources with quasi-monochromatic excitation radiation are arranged at one location or at different locations in a radiation area, the indicator with a plurality of indicator substances in an indicator area can be impinged upon by excitation radiation at different locations and/or different times for producing the emission, the emission is receivable for one location or different locations of a reception area, the entrance area of a wavelength-selective device can be impinged upon by the emission received in the reception area and one or more receivers for receiving emissions are arranged in an exit area of the wavelength-selective device, wherein the radiation area, the indicator area and the reception area are spaced apart in a defined manner and the apparatus is configured in such a way that the emissions in the entrance area of the wavelength-selective device are spatially and/or temporally decoupled in such a way that the emissions are resolvable by the wavelength-selective device without mutual superposition of emissions.

The optical apparatus for generating and measuring emissions is preferably situated within a robust housing with a display, not illustrated in any more detail, in the case of primed assembled appliances. A coupled indicator may be situated in the same housing or in a separate dedicated housing that can be removed from the housing. An adsorption and desorption apparatus for guiding analytes, electronics and an autonomous, non-wired energy supply (battery or accumulator) may also be held in the housing. In preferred embodiments, the entire system is embodied as an easily transportable, compact hand-held appliance which is largely insensitive to disturbances due to shocks and vibrations. It is dust-tight and water-tight and can be operated reliably over a large temperature range.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A portable appliance for detecting explosive materials, comprising:
   an apparatus for generating and measuring emission of an indicator, wherein
   the indicator has a carrier and a plurality of indicator substances that can be impinged upon by analytes,
   the indicator substances are applied onto the carrier as a thin layer and are positionable in an indicator area by a holding apparatus,
   the indicator substances are arranged in different regions of the carrier such that the indicator substances in the indicator area represent a pattern of indicator substances depending on the location,
   the apparatus comprising:
   a plurality of radiation sources configured to emit quasi-monochromatic excitation radiation,
   wherein the radiation sources are arranged at various locations in a radiation area such that the radiation area represents a pattern of radiation sources depending on the location;
   an excitation beam path comprising at least one first imaging system configured to image excitation radiation into the indicator area such that emission of the indicator substances is producible at the locations at which the excitation radiation is imaged on the indicator area;
   an emission beam path comprising at least one second imaging system configured to image the indicator area into a reception area such that a pattern of emissions is producible in the reception area depending on the location;
   a plurality of receivers configured to receive emissions from the reception area and to convert the received emissions into electrical signals, wherein
   the excitation beam path and the emission beam path are arranged in a backward geometry such that the excitation beam path and the emission beam path are arranged on one and the same side of the indicator area,
   a measurement geometry is set such that excitation radiation that has undergone specular reflection at the indicator does not strike the reception area, and
   different angles of excitation radiation and emission radiation in relation to the surface normal of the indicator are provided in the region where the excitation radiation strikes.

2. The appliance as claimed in claim 1, wherein optical axes of at least one first imaging system of the excitation beam path and at least one second imaging system of the emission beam path include an angle.

3. A portable appliance for detecting explosive materials, comprising:
an apparatus for generating and measuring emission of an indicator, wherein
the indicator has a carrier and a plurality of indicator substances that can be impinged upon by analytes,
the indicator substances are applied onto the carrier as a thin layer and are positionable in an indicator area by a holding apparatus,
the indicator substances are arranged in different regions of the carrier such that the indicator substances in the indicator area represent a pattern of indicator substances depending on the location,
the apparatus comprising:
a plurality of radiation sources configured to emit quasi-monochromatic excitation radiation,
wherein the radiation sources are arranged at various locations in a radiation area such that the radiation area represents a pattern of radiation sources depending on the location;
an excitation beam path comprising at least one first imaging system configured to image excitation radiation into the indicator area such that emission of the indicator substances is producible at the locations at which the excitation radiation is imaged on the indicator area;
an emission beam path comprising at least one second imaging system configured to image the indicator area into a reception area such that a pattern of emissions is producible in the reception area depending on the location;
a plurality of receivers configured to receive emissions from the reception area and to convert the received emissions into electrical signals, wherein
the excitation beam path and the emission beam path are arranged in a backward geometry such that the excitation beam path and the emission beam path are arranged on one and the same side of the indicator area, and
optical axes of one or more first imaging systems of the excitation beam path and one or more second imaging systems of the emission beam path cross at a distance in front of the indicator area so that points of intersection of the optical axes in the indicator area are laterally spaced apart.

4. The appliance as claimed in claim 3, wherein a separate receiver is assigned to each indicator substance.

5. The appliance as claimed in claim 4, wherein one or both of:
(i) interstices without light-sensitive areas lie between the receivers and (ii) the receivers are individually adjustable.

6. The appliance as claimed in claim 3, wherein one or more radiation sources are assigned to each indicator substance, and
a radiation source is assigned to at most one indicator substance so there are not two or more indicator substances that are assigned the same radiation source.

7. The appliance as claimed in claim 3, further comprising:
a clock configured to actuate radiation sources, wherein the clock is configured such that all radiation sources are clocked sequentially in series or that some of the radiation sources are clocked simultaneously or that all radiation sources are clocked simultaneously.

8. The appliance as claimed in claim 3, wherein all optical elements of the excitation beam path and of the emission beam path are integrated in a single component that acts as an optics holder for the optical elements.

9. The appliance as claimed in claim 3, wherein an indicator comprises at least one indicator substance which, in the case of irradiation by excitation radiation and contact with an analyte containing at least one explosive material, exhibits a reduction or increase in fluorescence intensity emitted by the indicator substance.

10. The appliance as claimed in claim 3 further, comprising at least one of the following features:
(i) the appliance is configured as a hand-held appliance such that the appliance is holdable by only one hand during use;
(ii) the appliance has a mass of less than 2 kilograms;
(iii) the appliance has an installation size, including the holding device for the indicator, of less than 50 cm measured in the direction of greatest extent;
(iv) the holding apparatus is attached in relation to the apparatus in such a way that the thin layer with indicator substances that is applied to the carrier of the indicator is positioned in the indicator area.

11. The use of the appliance as claimed in claim 3 for detecting explosive materials, wherein use is made of an indicator that has at least one indicator substance which, in the case of irradiation by excitation radiation and contact with an analyte containing at least one explosive material, exhibits a reduction or increase in the fluorescence intensity emitted by the indicator substance.

12. A portable appliance for detecting explosive materials, comprising:
an apparatus for generating and measuring emission of an indicator, wherein
the indicator has a carrier and a plurality of indicator substances that can be impinged upon by analytes,
the indicator substances are applied onto the carrier as a thin layer and are positionable in an indicator area by a holding apparatus,
the indicator substances are arranged in different regions of the carrier such that the indicator substances in the indicator area represent a pattern of indicator substances depending on the location,
the apparatus comprising:
a plurality of radiation sources configured to emit quasi-monochromatic excitation radiation,
wherein the radiation sources are arranged at various locations in a radiation area such that the radiation area represents a pattern of radiation sources depending on the location;
an excitation beam path comprising at least one first imaging system configured to image excitation radiation into the indicator area such that emission of the indicator substances is producible at the locations at which the excitation radiation is imaged on the indicator area;
an emission beam path comprising at least one second imaging system configured to image the indicator area into a reception area such that a pattern of emissions is producible in the reception area depending on the location;

a plurality of receivers configured to receive emissions from the reception area and to convert the received emissions into electrical signals, wherein the excitation beam path and the emission beam path are arranged in a backward geometry such that the excitation beam path and the emission beam path are arranged on one and the same side of the indicator area, the excitation beam path has a plurality of excitation channels, and each excitation channel has a first imaging system that defines an optical axis of the excitation channel.

13. The appliance as claimed in claim 12, wherein
the emission beam path has a common second imaging system for all emissions, said second imaging system defining an optical axis of the emission beam path.

14. The appliance as claimed in claim 13, wherein
the excitation channels form a symmetric arrangement in relation to the emission channel, and the arrangement is mirror symmetric in relation to at least one symmetry plane that contains the optical axis of the emission beam path.

15. The appliance as claimed in claim 14 wherein
the optical axes of the excitation channels and the optical axis of the emission channel cross at a distance in front of the indicator area so that points of intersection of the optical axes in the indicator area are laterally spaced apart.

16. The appliance as claimed in claim 13, wherein
the excitation channels and the emission channel form a conical arrangement, and optical axes of the excitation channels are arranged on a lateral conical face that surrounds the emission channel and the optical axis of the emission channel is arranged along the axis of the conical face.

17. The appliance as claimed in claim 12, wherein
each indicator region has exactly one excitation channel so that the number of excitation channels corresponds to the number of indicator regions.

18. A portable appliance for detecting explosive materials, comprising:

an apparatus for generating and measuring emission of an indicator, wherein the indicator has a carrier and a plurality of indicator substances that can be impinged upon by analytes, the indicator substances are applied onto the carrier as a thin layer and are positionable in an indicator area by a holding apparatus, the indicator substances are arranged in different regions of the carrier such that the indicator substances in the indicator area represent a pattern of indicator substances depending on the location, the apparatus comprising:

a plurality of radiation sources configured to emit quasi-monochromatic excitation radiation, wherein the radiation sources are arranged at various locations in a radiation area such that the radiation area represents a pattern of radiation sources depending on the location;

an excitation beam path comprising at least one first imaging system configured to image excitation radiation into the indicator area such that emission of the indicator substances is producible at the locations at which the excitation radiation is imaged on the indicator area;

an emission beam path comprising at least one second imaging system configured to image the indicator area into a reception area such that a pattern of emissions is producible in the reception area depending on the location;

a plurality of receivers configured to receive emissions from the reception area and to convert the received emissions into electrical signals;

at least one excitation channel that is assigned two or more radiation sources configured to emit different excitation wavelengths, wherein the radiation sources are alternately clockable by a clock; and a radiation merging device configured to selectively couple excitation radiation from the radiation sources into the excitation channel.

19. The appliance as claimed in claim 18, further comprising:

a beam shaper arranged in an excitation channel between a radiation source and the indicator plane, wherein the beam shaper is configured to convert a non-uniform intensity profile into a uniform and steep intensity profile.

20. A portable appliance for detecting explosive materials, comprising:

an apparatus for generating and measuring emission of an indicator, wherein the indicator has a carrier and a plurality of indicator substances that can be impinged upon by analytes, the indicator substances are applied onto the carrier as a thin layer and are positionable in an indicator area by a holding apparatus, the indicator substances are arranged in different regions of the carrier such that the indicator substances in the indicator area represent a pattern of indicator substances depending on the location, the apparatus comprising:

a plurality of radiation sources configured to emit quasi-monochromatic excitation radiation, wherein the radiation sources are arranged at various locations in a radiation area such that the radiation area represents a pattern of radiation sources depending on the location;

an excitation beam path comprising at least one first imaging system configured to image excitation radiation into the indicator area such that emission of the indicator substances is producible at the locations at which the excitation radiation is imaged on the indicator area;

an emission beam path comprising at least one second imaging system configured to image the indicator area into a reception area such that a pattern of emissions is producible in the reception area depending on the location;

a plurality of receivers configured to receive emissions from the reception area and to convert the received emissions into electrical signals, wherein the holding apparatus comprises a delivery air connector comprising an inlet opening for suctioning a gaseous medium that carries the searched-for analyte or analytes, the medium with the analytes is guidable over the indicator substances with the aid of a fluid channel system and is outputable from the holding apparatus after contact with said indicator substances by way of an exhaust air connector; and the holding apparatus comprises a heater configured to heat the suctioned medium prior to contact with the indicator substances.

21. The appliance as claimed in claim 20, further comprising:
an evaluation device, connected to the receivers and configured to receive electrical signals of the receivers and to evaluate spectral information about the emissions contained in the signals, wherein
the evaluation device is configured such that at least one of the following information items is establishable and is outputtable to an operator:
(i) information items about the amount of one or more searched-for analytes,
(ii) information about the type of one or more analytes,
wherein the analytes comprise one or more explosive materials.

22. A portable appliance, comprising:
an apparatus configured to generate and measure emission of an indicator, wherein
the indicator has a carrier and a plurality of indicator substances that can be impinged upon by analytes,
the indicator substances are applied onto the carrier as a thin layer and are positionable in an indicator area by a holding apparatus,
the indicator substances are arranged in different regions of the carrier in such a way that the indicator substances in the indicator area represent a spatial pattern of indicator substances,
the apparatus comprising:
a plurality of radiation sources each configured to emit quasi-monochromatic excitation radiation, the radiation sources being arranged at various locations in a radiation area such that the radiation area represents a spatial pattern of radiation sources;
an excitation beam path comprising a plurality of excitation channels, wherein each excitation channel has a first imaging system that defines an optical axis of the excitation channel and is configured to image excitation radiation into the indicator area such that emission of the indicator substances is producible at the locations at which the excitation radiation is imaged on the indicator area;
an emission beam path comprising a common second imaging system for all emissions, said second imaging system defining an optical axis of the emission beam path and being configured to image the indicator area into a reception area such that a spatial pattern of emissions is producible in the reception area, wherein
the excitation beam path and the emission beam path are arranged in a backward geometry on one and the same side of the indicator area,
the optical axes of the first imaging systems and the optical axis of the second imaging system cross at a distance in front of the indicator area so that points of intersection of the optical axes in the indicator area are laterally spaced apart;
a plurality of receivers configured to receive emissions from the reception area and to convert the received emissions into electrical signals,
wherein the appliance is configured to detect explosive materials.

* * * * *